United States Patent [19]

Rathmell et al.

[11] Patent Number: 5,395,987
[45] Date of Patent: Mar. 7, 1995

[54] PREPARATION OF CYCLOHEXANEDIMETHANOL WITH A PARTICULAR RATIO

[75] Inventors: Colin Rathmell, Yarm; Richard C. Spratt, South Harrow; Michael W. M. Tuck, London, all of England

[73] Assignee: Eastman Chemical Company, Kingsport, Tenn.

[21] Appl. No.: 175,502

[22] Filed: Dec. 30, 1993

[30] Foreign Application Priority Data

Dec. 2, 1993 [GB] United Kingdom ............... 9324752

[51] Int. Cl.$^6$ ................... C07C 31/13; C07C 27/04
[52] U.S. Cl. ................... 568/831; 568/822; 568/830; 568/862; 568/864
[58] Field of Search ............ 568/822, 830, 831, 864, 568/862, 861

[56] References Cited

U.S. PATENT DOCUMENTS

| | | | |
|---|---|---|---|
| 2,040,944 | 5/1936 | Lazier | 568/844 |
| 2,079,414 | 5/1937 | Lazier | 568/830 |
| 2,091,800 | 8/1937 | Adkins et al. | 568/864 |
| 2,105,664 | 1/1938 | Lazier | 568/864 |
| 2,137,407 | 11/1938 | Lazier | 568/864 |
| 2,755,317 | 7/1956 | Kassel | 585/654 |
| 2,818,393 | 12/1957 | Lefrancois et al. | 502/100 |
| 2,830,095 | 4/1958 | Nicolaisen | 570/231 |
| 2,884,450 | 4/1959 | Holmquist | 568/880 |
| 2,901,466 | 8/1959 | Kibler et al. | 568/830 |
| 2,917,549 | 5/1959 | Hasek et al. | 568/830 |
| 3,334,149 | 8/1967 | Akin et al. | 568/830 |
| 4,032,458 | 6/1977 | Cooley et al. | 568/830 |
| 4,052,467 | 10/1977 | Mills et al. | 568/880 |
| 4,172,961 | 10/1979 | Henery et al. | 568/864 |
| 4,268,695 | 5/1981 | Lange et al. | 568/864 |
| 4,361,710 | 11/1982 | Weitz et al. | 568/864 |
| 4,584,419 | 4/1986 | Sharif et al. | 568/864 |
| 4,652,685 | 5/1987 | Cawse et al. | 568/864 |
| 4,751,334 | 6/1988 | Turner et al. | 568/864 |

(List continued on next page.)

FOREIGN PATENT DOCUMENTS

143634 6/1985 European Pat. Off. .
241760 10/1987 European Pat. Off. .
301853 2/1989 European Pat. Off. .

(List continued on next page.)

OTHER PUBLICATIONS

Mansour et al., "Sel. Hydrog. of Esters to Alcoh. with a Catal. Obtained Rh$_2$O$_3$, Sn(n–C$_4$H$_9$)$_4$ and SiO$_2$ and Based on Isol. Active Centres", *Angew. Chem.* 101, (1989), No. 3, 360–63.

(List continued on next page.)

*Primary Examiner*—Werren B. Lone
*Attorney, Agent, or Firm*—J. Frederick Thomsen; Harry J. Gwinnell

[57] ABSTRACT

A continuous process is described for the production of 1,4-cyclohexanedimethanol (CHDM) having a desired or predetermined trans-:cis- isomer ratio by catalytic hydrogenation of a dialkyl 1,4-cyclohexanedicarboxylate in the presence of an ester hydrogenation catalyst. The process is capable of being operated for an extended period of time during which the hydrogenation catalyst declines in catalytic activity and comprises feeding a vaporous mixture of the dialkyl 1,4-cyclohexanedicarboxylate and hydrogen to a hydrogenation zone containing the hydrogenation catalyst and recovering CHDM product. The degree of conversion of the dialkyl 1,4-cyclohexanedicarboxylate at a particular combination of temperature and pressure is related to the trans-:cis- isomer ratio of the CHDM product and may be varied by adjusting at least one feed condition selected from (i) the dialkyl 1,4-cyclohexanedicarboxylate feed rate and (ii) the hydrogen-containing gas:dialkyl 1,4-cyclohexanedicarboxylate molar ratio. As catalyst activity declines during operation of the process over an extended period of time at a particular combination of temperature and pressure, the degree of conversion of the dialkyl 1,4-cyclohexanedicarboxylate and/or the trans-:cis- isomer ratio of the CHDM product may be maintained at a constant value by adjusting at least one of the feed conditions referred to above. The determination of the Actual Activity and Reference Activity of the catalyst and the Actual and Effective Residence Times are included in the hydrogenation process.

15 Claims, 3 Drawing Sheets

U.S. PATENT DOCUMENTS

| | | | |
|---|---|---|---|
| 4,837,368 | 6/1989 | Gustafson et al. | 568/881 |
| 4,929,777 | 5/1990 | Irick, Jr. et al. | 568/864 |
| 4,999,090 | 3/1991 | Tateno et al. | 203/36 |
| 5,030,771 | 7/1991 | Fuhrmann et al. | 568/830 |
| 5,124,435 | 6/1992 | Mori et al. | 528/307 |
| 5,142,067 | 8/1992 | Wegman et al. | 549/326 |
| 5,185,476 | 2/1993 | Gustafson | 568/831 |
| 5,191,091 | 3/1993 | Wegman et al. | 549/326 |

FOREIGN PATENT DOCUMENTS

| | | |
|---|---|---|
| 353990 | 2/1990 | European Pat. Off. . |
| 378756 | 7/1990 | European Pat. Off. . |
| 552463 | 7/1993 | European Pat. Off. . |
| 1276722 | 10/1961 | France . |
| 1144703 | 3/1963 | Germany . |
| 1159925 | 12/1963 | Germany . |
| 2719867 | 11/1978 | Germany . |
| 3843956 | 6/1990 | Germany . |
| 4141199 | 6/1993 | Germany . |
| 988316 | 4/1965 | United Kingdom . |
| 1024318 | 3/1966 | United Kingdom . |
| 1454440 | 11/1976 | United Kingdom . |
| 1464263 | 2/1977 | United Kingdom . |
| 2116552 | 9/1985 | United Kingdom . |
| 2250287 | 6/1992 | United Kingdom . |
| 8203854 | 11/1982 | WIPO . |
| 8603189 | 6/1986 | WIPO . |
| 8607358 | 12/1986 | WIPO . |
| 8800937 | 2/1988 | WIPO . |
| 8900886 | 2/1989 | WIPO . |
| 9008121 | 7/1990 | WIPO . |
| 9101961 | 2/1991 | WIPO . |

OTHER PUBLICATIONS

Wehner & Gustafson, "Catalytic Hydrog. of Esters Over Pd/ZnO", *Journ. of Catalysts,* 135, 420–426 (1992).

Lewin et al., "Fiber Chemistry", pp. 8–9 (1985).

Martyn V. Twigg, "Catalyst Handbook", 2nd Ed., p. 54.

Homer Adkins, "Cataly. Hydrog. of Esters to Alcoh.", *Organic Reactions,* vol. 8, Chp. 1, pp. 2–27 (1954).

Freifelder, "Catal. Hydrog. in Org. Synth.", pp. 129–151.

Kirk-Othmer, *Encl. of Chem. Tech.,* 3rd Ed., vol. 1, pp. 733–739.

PREPARATION OF CYCLOHEXANEDIMETHANOL WITH A PARTICULAR RATIO

FIELD OF THE INVENTION

This invention relates to a process for the production of 1,4-cyclohexanedimethanol.

BACKGROUND OF THE INVENTION 1,4-cyclohexanedimethanol is used to prepare highly polymeric linear condensation polymers by reaction with terephthalic acid and is useful as an intermediate in the preparation of certain polyester and polyester amides. The use of 1,4-cyclohexanedimethanol for such purposes is disclosed in, for example, U.S. Pat. No. 2,901,466. This document teaches that the trans-isomer of polycyclohexylenedimethylene terephthalate has a higher melting point range (315°–320° C.) than the corresponding cis-isomer (260°–267° C.).

One method for preparing 1,4-cyclohexanedimethanol (hexahydroterephthalyl alcohol) involves the hydrogenation of diethyl 1,4-cyclohexanedicarboxylate (diethyl hexahydroterephthalate) in a slurry phase reactor in the presence of a copper chromite catalyst at a pressure of 3000 psia (about 206.84 bar) and a temperature of 255° C., as is described in Example 3 of U.S. Pat. No. 2,105,664. The yield is said to be 77.5%.

The hydrogenation of dimethyl 1,4-cyclohexanedicarboxylate (DMCD) to 1,4-cyclohexanedimethanol (CHDM) is shown below in equation (1):-

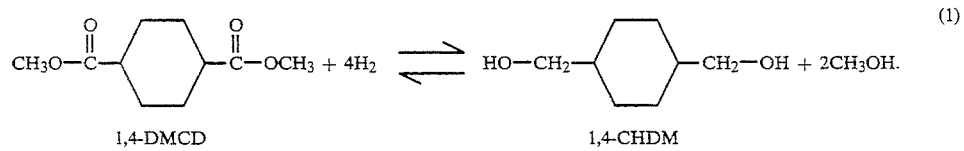

1,4-DMCD    1,4-CHDM

The two geometrical isomers of CHDM thus produced are:

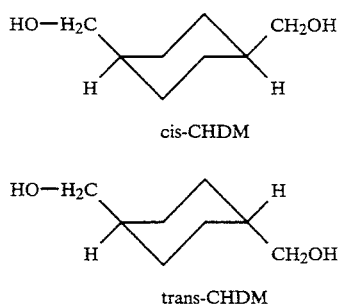

cis-CHDM trans-CHDM

The resulting 1,4-cyclohexanedimethanol product is a mixture of these two isomers which have different melting points. As reported on page 9 of the book "Fiber Chemistry" edited by Menachem Lewis and Eli M. Pearce, published by Marcel Dekker, Inc.: "Both the alicyclic ester [i.e. dimethyl 1,4-cyclohexanedicarboxylate] and the alicyclic diol [i.e.1,4-cyclohexanedimethanol] exist in two isomeric forms, cis ... and trans ..., that are not interconvertible without bond rupture". The passage continues later: "Control of the [cis-:trans-] ratio is important [in 1,4-cyclohexanedimethanol] since many polymer and fiber properties depend on it".

The cis-isomer of 1,4-cyclohexanedimethanol has a melting point of 43° C. and the trans has a melting point of 67° C. The higher melting point trans-isomer is often preferred over the cis-isomer for use as a reagent in the preparation of polyester and polyester-amides if a high melting point for such materials is considered desirable. As noted above, the trans-isomer of a typical polyester, such as trans-polycyclohexylmethyl terephthalate, has a higher melting point than the cis-isomer. Hence, for example, U.S. Pat. No. 5,124,435 discloses a polyester copolymer, the 1,4-cyclohexanedimethanol content of which has a trans-isomer content of at least 80 mole %, and which has a high heat resistance. The preferment of trans-1,4-cyclohexanedimethanol over cis-1,4-cyclohexanedimethanol is also discussed in U.S. Pat. No. 2,917,549, in U.S. Pat. No. 4,999,090 and in GB-A988316.

A liquid phase process for the production of 1,4-cyclohexanedimethanol by plural stage hydrogenation of dimethyl terephthalate is described in U.S. Pat. No. 3,334,149. This utilises a palladium catalyst to effect hydrogenation of dimethyl terephthalate to dimethyl 1,4-cyclohexanedicarboxylate, followed by use of a copper chromite catalyst in the liquid phase to catalyse the hydrogenation of that diester to 1,4-cyclohexanedimethanol. In the procedure described in Example 1 of that patent specification a residence time of about 40 to 50 minutes is used in the second stage of this process. The activity of the copper chromite catalysts recommended in U.S. Pat. No. 3,334,149 is such that long residence times are required.

In a liquid phase process for the production of 1,4-cyclohexanedimethanol, such as is disclosed in U.S. Pat. No. 3,334,149, the trans-:cis- isomer ratio of the product 1,4-cyclohexanedimethanol will tend towards an equilibrium value. This equilibrium value has been reported variously and may lie between about 2.57:1 (trans-:cis- 1,4-cyclohexanedimethanol) (as reported in GB-A-988316) and about 3:1 (as reported in U.S. Pat. No. 2,917,549). However, the starting material, dimethyl 1,4-cyclohexanedicarboxylate, is generally commercially obtainable as a mixture of cis- and trans-isomers wherein there is a preponderance of the cisisomer. Thus in a typical commercial grade of dimethyl 1,4-cyclohexanedicarboxylate the trans-:cis- isomer ratio is from about 0.5:1 to about 0.6:1. Moreover, the rate of approach to the equilibrium product composition during the hydrogenation process is slow in the liquid phase. Liquid phase hydrogenation of a typical commercial grade of dimethyl 1,4-cyclohexanedicarboxylate according to the teaching of the prior art therefore provides a process wherein the rate of approach to the appropriate trans-:cis- isomer equilibrium ratio for 1,4-cyclohexanedimethanol, reported to be about between 2.57:1 and about 3:1, is very slow. Hence in a commercial liquid phase process the requirement, in terms of operating and catalyst consumption costs, for high reactor throughput conflicts with the requirement for a product which contains a high proportion of the trans-isomer.

Attempts to deal with the problem of the presence of an excess of the less desirable cis-1,4-cyclohexanedimethanol isomer in any process for 1,4-cyclohexanedimethanol manufacture have focused on the isomerisation of the cis- isomer of cyclohexanedimethanol to the trans-isomer thereof.

U.S. Pat. No. 2,917,549 discloses a process for isomerising cis-1,4-cyclohexanedimethanol to trans-1,4-cyclohexanedimethanol which comprises heating cis-1,4-cyclohexanedimethanol at a temperature of at least 200° C. in the presence of an alkoxide of a lower atomic weight metal such as lithium, sodium, potassium, calcium or aluminium. However, the process of U.S. Pat. No. 2,917,549 necessarily involves a two-stage process wherein the initial cis-/trans- 1,4-cyclohexanedimethanol hydrogenation product is recovered from the hydrogenation zone and subjected to temperatures in excess of 200° C. in the presence of a metal alkoxide catalyst under an atmosphere of nitrogen. The capital and operational costs associated with a plant designed to carry out the process taught in U.S. Pat. No. 2,917,549 would be undesirably high. Another disadvantage of such a plant is the associated hazard relating to the use of metal alkoxides as catalysts in the isomerisation zone. Such catalysts are required to effect the isomerisation, which is reported not to occur under typical hydrogenation conditions using hydrogenation catalysts such as copper/chrome or Raney nickel catalysts, according to the teaching of Example 11 of U.S. Pat. No. 2,917,549. Furthermore, steps would be required to prevent product contamination by the metal alkoxide catalyst.

U.S. Pat. No. 4,999,090 discloses a process for the isomerisation of cis-1,4-cyclohexanedimethanol by distillation in the presence of an alkali metal hydroxide or alkoxide at a temperature of between 150° C. and 200° C. and at a pressure of between 1 mm Hg and 50 mm Hg (between 1.33 millibar and 66.5 millibar). This process has very similar disadvantages to those of U.S. Pat. No. 2917549.

GB-A-988316 teaches a process for the preparation of trans-1,4-cyclohexanedimethanol in which a mixture of cis- and trans-isomers of dimethyl hexahydroterephthalate (i.e. dimethyl 1,4-cyclohexanedicarboxylate) is hydrogenated at elevated temperature and pressure in the presence of a Cu/Zn catalyst. Trans-1,4-dimethylolcyclohexane (i.e. trans-1,4-cyclohexanedimethanol) is separated by crystallisation from the reaction product and then the residual product, now enriched in cis-1,4-cyclohexanedimethanol, is recycled to the hydrogenation zone whereupon it undergoes isomerisation to a cis-/trans- 1,4-cyclohexanedimethanol mixture. The recycle procedure may be repeated to obtain a 1,4-cyclohexanedimethanol product containing the trans-isomer in substantial excess. However, the process according to GB-A-988316 is more preferably operated under conditions such that recycled cis-isomer enriched product is combined with fresh dimethyl 1,4-cyclohexanedicarboxylate feed on re-entry to the hydrogenation zone. The effectiveness of recycling the cis-isomer to the hydrogenation zone is largely a result of the dual function of the copper/zinc catalyst which possesses both a hydrogenating and an isomerising catalytic action. As would be expected from thermodynamic principles, the isomerising action is most effective when a mixture containing a preponderance of the cis-isomer is recycled to the hydrogenation zone. However, recycling the cis-isomer in this way is acknowledged to cause a new problem, that of the formation of unwanted by-products, such as 1-methyl-4-hydroxymethylcyclohexane, which may be formed by operating the hydrogenation reaction under too severe conditions. To minimise the formation of such by-products, the hydrogenation zone may be operated under "relatively mild conditions", according to the teaching of GB-A-988316 (see, for example page 2, lines 55 to 79 of GB-A-988316). However, such mild conditions reduce the achieved conversion of dimethyl 1,4-cyclohexanedicarboxylate with the result that, for any one pass through the hydrogenation zone, a significant quantity of dimethyl hexahydroterephthalate (dimethyl 1,4-cyclohexanedicarboxylate) remains unconverted. By the term "relatively mild conditions" is meant a temperature of at least 200° C., preferably between 240° C. and 300° C., and a pressure of 200 to 300 atmospheres (202.65 bar to 303.98 bar), according to page 2, lines 26 to 32 of GB-A988316. The use of such high pressures at these elevated temperatures can be hazardous, besides requiring reactors with thick walls and flanges of special alloy constructed to withstand such extreme pressures. Hence it is expensive to construct a plant to operate at pressures as high as envisaged in GB-A-988316. Furthermore it is potentially hazardous to operate a plant operating at 200 atmospheres (202.65 bar) or above, as well as being very expensive, not only in terms of the capital cost of the plant but also with regard to operating costs. A substantial proportion of this capital cost is associated with the rigorous safety precautions that must be taken when operating a high pressure conventional commercial scale hydrogenation plant. It is also expensive to compress gaseous streams to such high pressures and to circulate them through the plant.

Although there is a passing reference (see page 1, line 84 of GB-A-988316) to use of "the gaseous phase", even at temperatures of 300° C. both cis- and trans- dimethyl hexahydroterephthalate would be in the liquid phase at pressures of 200 to 300 atmospheres (202.65 bar to 303.98 bar) at the hydrogen:ester ratio envisaged in the Examples. Thus in each of the Examples of GB-A-988316 liquid phase conditions are used. According to Example 4, which uses a feed mixture containing dimethyl hexahydroterephthalate (i.e. 1,4-dimethyl cyclohexanedicarboxylate), and methanol such as might be used in a recycling process, the isomers present in the diol in the hydrogenation product are stated to represent an equilibrium mixture of about 72% of the trans- and about 28% of the cis-isomer, i.e. a trans-:cisratio of about 2.57:1.

It is known to effect hydrogenation of certain esters and diesters in the vapour phase. For example it has been proposed to use a reduced copper oxide/zinc oxide catalyst for effecting hydrogenation of esters in the vapour phase. In this connection attention is directed to GB-B2116552. Also of relevance is WO-A-90/8121.

It is further known to produce diols, such as butane-1,4-diol, by catalytic hydrogenation of esters of dicarboxylate acids, such as a dimethyl or diethyl ester of maleic acid, fumaric acid, succinic acid, or a mixture of two or more thereof. Such processes are described, for example, in GB-A-1454440, GB-A-1464263, DE-A-2719867, U.S. Pat. No. 4,032,458, and U.S. Pat. No. 4172961.

Production of butane-1,4-diol by vapour phase hydrogenation of a diester, typically a dialkyl ester, of a C$_4$ dicarboxylic acid selected from maleic acid, fumaric acid, succinic acid, and a mixture of two or more thereof has been proposed. In such a process the diester is conveniently a di-(C$_1$ to C$_4$ alkyl) ester, such as dimethyl or diethyl maleate, fumarate, or succinate. A further description of such a process can be found in U.S. Pat. No. 4,584,419, EP-A-0143634, WO-A-86/03189, WO-A-86/07358, and WO-A-88/00937.

In all of the above-mentioned vapour phase processes the esters or diesters all have a vapour pressure which is high compared to the vapour pressure of dimethyl 1,4-cyclohexanedicarboxylate and 1,4-cyclohexanedimethanol.

SUMMARY OF THE INVENTION

It is accordingly an object of the present invention to provide a process for the production of cyclohexanedimethanol by hydrogenation of a dialkyl (e.g. dimethyl) cyclohexanedicarboxylate which can be operated with substantially increased safety and operating economy at relatively low pressures. Another object of the invention is to provide a process for production of 1,4-cyclohexanedimethanol by hydrogenation of a di-(C$_1$ to C$_4$alkyl) cyclohexanedicarboxylate, such as dimethyl 1,4-cyclohexanedicarboxylate, wherein the hydrogenation step yields directly a 1,4-cyclohexanedimethanol product with a higher trans-:cis- isomer ratio than is achievable by conventional hydrogenation methods. Hence it is a still further object of the invention to avoid the increased capital and operating costs of the prior art processes mentioned above which require the use of extreme hydrogenation conditions or a separate isomerisation step. It is also an object of the present invention to provide a process wherein a mixture of cis- and trans- isomers of dimethyl 1,4-cyclohexanedicarboxylate is reacted rapidly with high conversion and high selectivity to a mixture of cis- and trans-isomers of 1,4-cyclohexanedimethanol wherein the trans-isomer is present in excess of the cis-isomer. An additional object of the invention is to provide a process for the production of 1,4-cyclohexanedimethanol which can be operated so that a product having a particular desired trans-:cis- isomer ratio, which may be changed at will from time to time, can be produced from a given dimethyl 1,4-cyclohexanedicarboxylate feedstock. One more object of the invention is to provide a process for the production of a cyclohexanedimethanol product having a desired trans-:cis- isomer ratio from a variety of dimethyl cyclohexanedicarboxylate feedstocks having different trans-:cis- isomer ratios in the feedstocks. Yet another object of the present invention is to provide a process for the production of 1,4-cyclohexanedimethanol which can be operated for extended periods of time during which the hydrogenation catalyst can lose activity whilst continuing to yield a product with a substantially constant desired trans-:cis ratio.

According to the present invention there is provided a continuous process for the production of 1,4-cyclohexanedimethanol having a desired or predetermined trans-:cis- isomer ratio by catalytic hydrogenation of a dialkyl 1,4-cyclohexanedicarboxylate in the presence of an ester hydrogenation catalyst, which process is capable of being operated for an extended period of time during which the hydrogenation catalyst declines in catalytic activity, said process comprising:

(a) providing a hydrogenation zone containing a charge of a granular hydrogenation catalyst capable of catalysing the hydrogenation of esters;
(b) determining a Reference Activity (RA) of the granular hydrogenation catalyst by measuring the extent of conversion of the dialkyl 1,4-cyclohexanedicarboxylate to 1,4-cyclohexanedimethanol in passage of a reaction mixture comprising the dialkyl 1,4-cyclohexanedicarboxylate and a hydrogen-containing gas through the granular hydrogenation catalyst at a preselected feed temperature, feed pressure, dialkyl 1,4-cyclohexanedicarboxylate feed rate, and hydrogen-containing gas:dialkyl 1,4-cyclohexanedicarboxylate molar ratio;
(c) determining an Effective Residence Time (ERT) for contact of the reaction mixture at the preselected feed temperature and feed pressure with the granular hydrogenation catalyst at the reference activity thereof which produces 1,4-cyclohexanedimethanol having the desired trans-:cis- isomer ratio;
(d) forming a vaporous feed stream comprising the dialkyl 1,4-cyclohexanedicarboxylate and a hydrogen-containing gas having a preselected hydrogen-containing gas:dialkyl 1,4-cyclohexanedicarboxylate molar ratio;
(e) feeding the vaporous feed stream to the hydrogenation zone at a substantially constant temperature of from about 150° C. to about 350° C. and which is above the dew point of the feed stream and at a substantially constant pressure in the range of from about 150 psia (about 10.34 bar) to about 2000 psia (about 137.90 bar) at a rate which corresponds to an Actual Residence Time (ART) of the feed stream in contact with the catalyst which yields 1,4-cyclohexanedimethanol of the desired trans-:cis- isomer ratio;
(f) recovering from the hydrogenation zone a product stream containing 1,4-cyclohexanedimethanol;
(g) monitoring the Actual Activity (AA) of the granular hydrogenation catalyst with passage of time by measuring the extent of conversion of the dialkyl 1,4-cyclohexanedicarboxylate to 1,4-cyclohexanedimethanol under the actual operating conditions of feed temperature, feed pressure, dialkyl 1,4-cyclohexanedicarboxylate feed rate, and hydrogen-containing gas:dialkyl 1,4-cyclohexanedicarboxylate molar ratio; and
(h) adjusting at least one feed condition of the vaporous feed stream to the hydrogenation zone selected from
 (i) the dialkyl 1,4-cyclohexanedicarboxylate feed rate and
 (ii) the hydrogen-containing gas:dialkyl 1,4-cyclohexanedicarboxylate molar ratio while maintaining the feed stream above its dew point to provide an Actual Residence Time (ART) of the vaporous feed stream in contact with the catalyst which corresponds to the Effective Residence Time (ERT) required to provide 1,4-cyclohexanedimethanol having the desired trans-:cis- isomer ratio in accordance with the relationship:

$$ART = \frac{ERT \times RA}{AA}.$$

As used herein, the term "residence time" means the time taken for the vaporous feed stream at the feed temperature and feed pressure to the hydrogenation zone to pass through the empty volume of reactor occupied by the catalyst.

The choice of preselected feed conditions under which to determine the Reference Activity (RA) is at the discretion of the person skilled in the art. It is convenient to use for this purpose a set of feed conditions which approximates to the set of feed conditions to be used at the beginning of catalyst life.

In practice the activity of the catalyst may not be the same at any given time throughout the catalyst charge. However, what matters to the plant operator in selecting appropriate operating conditions is the overall activity of the catalyst charge. A convenient yardstick of the activity of a catalyst charge is the extent of conversion of the dialkyl 1,4-cyclohexanedicarboxylate in the reaction mixture in passage through the catalyst charge. Changes in the extent of conversion under substantially constant reaction conditions in the hydrogenation zone betoken a change in the activity of the catalyst charge. Thus, for example, if the extent of conversion of the dialkyl 1,4-cyclohexanedicarboxylate falls from 95% under a given set of operating conditions to 90% with passage of time and the operating conditions are not changed, then it can be said for the purposes of the present invention that the catalyst charge has lost half its activity. If the conversion under particular conditions at the reference activity is 99% and the conversion later drops to 97%, then the percentage of unconverted dialkyl 1,4-cyclohexanedicarboxylate has tripled and the actual activity of the catalyst charge at that later time will be 0.33, taking the reference activity as 1.0.

The dialkyl 1,4-cyclohexanedicarboxylate preferably is a di-($C_1$ to $C_4$ alkyl) 1,4-cyclohexanedicarboxylate, such as dimethyl, diethyl, di-n- or -iso-propyl, or di-n-, -iso- or -sec-butyl 1,4-cyclohexanedicarboxylate, or, more preferably, dimethyl 1,4-cyclohexanedicarboxylate.

The invention is predicated on the discovery that, at a given temperature and pressure, the rates of hydrogenation of the dialkyl 1,4-cyclohexanedicarboxylate and isomerisation of 1,4-cyclohexanedimethanol are substantially the same, so that at a given conversion of dialkyl 1,4-cyclohexanedicarboxylate one will achieve a 1,4-cyclohexanedimethanol product having a given trans-:cis- isomer ratio. The benefits afforded by the invention include the ability (1) to maintain a constant trans-:cis- isomer ratio in the 1,4-cyclohexanedimethanol product throughout the operating life of the catalyst and (2) to vary the trans-:cis-isomer ratio in the 1,4-cyclohexanedimethanol product over a wide range, e.g. from about 1:1 to about 3.84:1. Thus, not only is the conversion of the dialkyl 1,4-cyclohexanedicarboxylate to the 1,4-cyclohexanedimethanol, extremely rapid under the vapour phase hydrogenation conditions used, requiring only a matter of a few seconds for substantially complete conversion to occur, but also the approach of the isomerisation of 1,4-cyclohexanedimethanol to equilibrium that occurs in passage through the hydrogenation zone is comparably rapid. This is a surprising finding since two separate reactions are involved. Thus a close approach to the equilibrium trans-:cis- 1,4-cyclohexanedimethanol ratio, at a constant temperature, as well as essentially complete conversion of dialkyl 1,4-cyclohexanedicarboxylate to 1,4-cyclohexanedimethanol, can be achieved by using a residence time of less than about a minute of the reaction mixture in the hydrogenation zone, typically in the range of from about 2 to about 15 seconds. This residence time is in stark contrast to the extended residence times recommended in the liquid phase hydrogenation processes of the prior art, such as the 40 to 50 minutes residence time used in Example 1 of U.S. Pat. No. 3,334,149.

The process of the invention is operated using vaporous feed conditions with the feed stream being fed to the hydrogenation zone in step (e) in essentially liquid free vaporous form. Hence the feed stream is fed to the hydrogenation zone at a feed temperature which is above the dew point of the mixture. The process can be operated so that vapour phase conditions will exist throughout the hydrogenation zone. However, when using dimethyl 1,4-cyclohexanedicarboxylate as starting material, the product, 1,4-cyclohexanedimethanol, is less volatile than the starting material, dimethyl 1,4-cyclohexanedicarboxylate. Thus there is, in this case, the possibility of condensation of a 1,4-cyclohexanedimethanol-rich liquid occurring on the catalyst, particularly if the temperature of the feed stream is close to its dew point. Such condensation of a 1,4-cyclohexanedimethanol-rich liquid on the catalyst is not deleterious in the process of the invention because the heat of hydrogenation of any dimethyl 1,4-cyclohexanedicarboxylate present in the 1,4-cyclohexanedimethanol-rich liquid can be dissipated by the heat sink effect of the 1,4cyclohexanedimethanol. However, it is essential that the feed stream be at a temperature above its dew point at the inlet end of the catalyst bed if the advantage of vapour phase feed conditions is to be realised. The use of vapour phase feed conditions in the process of the invention has the advantage that, compared with liquid phase operation of the process, generally lower operating pressures can be used. This generally has a significant and beneficial effect not only on the construction costs but also on the operating costs of the plant.

Care has to be taken that contact of droplets of a dimethyl 1,4-cyclohexanedicarboxylate-rich liquid with the catalyst is avoided because this can cause severe localised overheating of, and damage to, the catalyst due to the exothermic nature of the ester hydrogenation reaction. In conventional liquid phase hydrogenation processes this danger is obviated by flooding the catalyst with liquid and by feeding the dimethyl 1,4-cyclohexanedicarboxylate to the hydrogenation zone in admixture with an inert diluent, conveniently 1,4-cyclohexanedimethanol.

In the hydrogenation zone the hydrogenatable material undergoes extremely rapid hydrogenation to yield 1,4-cyclohexanedimethanol according to equation (1) above. In addition, a fast isomerisation reaction occurs under the hydrogenation conditions used. Hence a feedstock rich in cis-dimethyl 1,4-cyclohexanedicarboxylate tends to yield a 1,4-cyclohexanedimethanol product that has a higher content of the trans-isomer thereof than the trans-content of the diester starting material. If the hot reaction mixture is passed over the hydrogenation catalyst at a suitable rate, then the trans-:cis- isomer ratio of the 1,4-cyclohexanedimethanol present in the reaction product mixture approaches the equilibrium value for vapour phase hydrogenation conditions. In the case of hydrogenation of dimethyl 1,4-cyclohexanedicarboxylate we have found that this equilibrium ratio is in the region of 3.84:1. This ratio is significantly higher than the ratio of between 2.57:1 and 3:1 which is reported to be achieved under liquid phase reaction conditions when using a cis-rich dimethyl 1,4-cyclohexanedicarboxylate as feedstock.

If the hydrogenatable material comprises substantially pure trans-dimethyl 1,4-cyclohexanedicarboxylate, then some cis-1,4-cyclohexanedimethanol will be formed. In this case the trans-:cis-isomer ratio of the resulting 1,4-cyclohexanedimethanol product may be higher than about 3.84:1 but will tend toward the equilibrium trans-:cis-isomer ratio, i.e. about 3.84:1, with increasing residence time in the hydrogenation zone.

The dialkyl 1,4-cyclohexanedicarboxylate supplied to the hydrogenation zone may comprise substantially pure cis-dimethyl 1,4-cyclohexanedicarboxylate, trans-dimethyl 1,4-cyclohexanedicarboxylate, or a mixture of the cis- and trans- isomers thereof in any ratio. The molar ratio of trans-dimethyl 1,4-cyclohexanedicarboxylate to cis-dimethyl 1,4-cyclohexanedicarboxylate in any such mixture may be in the range of from about 0.01:1 to about 1000:1, preferably in the range of from about 0.05:1 to about 1:1.

Dimethyl 1,4-cyclohexanedicarboxylate is commercially available as high purity dimethyl 1,4-cyclohexanedicarboxylate, technical grade dimethyl 1,4-cyclohexanedicarboxylate, cis-dimethyl 1,4-cyclohexanedicarboxylate, or trans-dimethyl 1,4-cyclohexanedicarboxylate. The preferred feedstock for the process of the invention is technical grade dimethyl 1,4-cyclohexanedicarboxylate, as the high purity, cis-, and trans- grades of dimethyl 1,4-cyclohexanedicarboxylate require additional purification stages in the course of their production. In a typical bulk sample of commercially available dimethyl 1,4-cyclohexanedicarboxylate the trans-:cis- isomer ratio is from about 0.5:1 to about 0.6:1.

When designing a plant to operate according to the teachings of the present invention it is necessary to decide on the volume of catalyst to be used for a projected production rate of a 1,4-cyclohexanedimethanol product having a trans-:cis- isomer ratio which corresponds to a desired approach to the equilibrium value of about 3.84:1. This volume will normally be selected to be sufficient to provide the desired extent of conversion in order that the trans-:cis- isomer ratio in the 1,4-cyclohexanedimethanol product shall achieve that desired approach not only at the beginning of the campaign when the catalyst can be expected to be at its most active but also at the end of the useful life of the catalyst. Placing the hydrogenation catalyst in two or more hydrogenation zones which can be operated singly, in series, or in parallel will give the plant operator the greatest flexibility. In selecting a suitable catalyst volume the plant designer should also consider the size of the gas supply compressor, the gas recycle compressor, and the associated pipework.

The hydrogen-containing gas used in the process may comprise fresh make-up gas or a mixture of make-up gas and recycle gas. The make-up gas can be a mixture of hydrogen, optional minor amounts of components such as CO and $CO_2$, and inert gases, such as argon, nitrogen, or methane, containing at least about 70 mole % of hydrogen. Preferably the make-up gas contains at least 90 mole %, and even more preferably at least 97 mole %, of hydrogen. The make-up gas can be produced in any convenient manner, e.g. by partial oxidation or steam reforming of natural gas followed by the water gas shift reaction, and $CO_2$ absorption, followed possibly by methanation of at least some of any residual traces of carbon oxides. Pressure swing absorption can be used if a high purity hydrogen make-up gas is desired. If gas recycle is utilised in the process then the recycle gas will normally contain minor amounts of one or more products of the hydrogenation reaction which have not been fully condensed in the product recovery stage downstream from the hydrogenation zone. Thus, when using gas recycle in the process of the invention, the gas recycle stream will typically contain a minor amount of an alkanol methanol).

The process of the invention is operated at a feed temperature of at least about 150° C. and no higher than about 350° C. The feed temperature is preferably in the range of from about 150° C. to about 300° C., most preferably from about 200° C. to about 260° C.

The feed pressure is in the range of from about 150 psia (about 10.34 bar) up to about 2000 psia (about 137.90 bar). However, the benefits and advantages of vapour phase feed conditions are best realised by using a feed pressure of from about 450 psia (about 31.03 bar) up to about 1000 psia (about 68.95 bar).

The process requires that the vaporous feed stream is above its dew point so that the dialkyl (e.g. dimethyl) 1,4-cyclohexanedicarboxylate is present in the vapour phase at the inlet end of the or each catalyst bed. This means that the composition of the vaporous feed mixture must be controlled so that, under the selected operating conditions, the temperature of the mixture at the inlet end of the or each catalyst bed is always above its dew point at the operating pressure. By the term "dew point" is meant that temperature at which a mixture of gases and vapours just deposits a fog or film of liquid. This dew point liquid will normally contain all the condensable components of the vapour phase, as well as dissolved gases, in concentrations that satisfy the usual vapour/liquid criteria. Typically the feed temperature of the vaporous feed mixture to the hydrogenation zone is from about 5° C. up to about 10° C. or more above its dew point at the operating pressure.

A convenient method of forming a vaporous mixture for use in the process of the invention is to spray liquid dimethyl 1,4-cyclohexanedicarboxylate or a dimethyl 1,4cyclohexanedicarboxylate solution into a stream of hot hydrogen-containing gas so as to form a saturated or partially saturated vaporous mixture. Alternatively such a vapour mixture can be obtained by bubbling a hot hydrogen-containing gas through a body of the liquid dimethyl 1,4cyclohexanedicarboxylate or dimethyl 1,4-cyclohexanedicarboxylate solution. If a saturated vapour mixture is formed it should then be heated further or diluted with more hot gas so as to produce a partially saturated vaporous mixture prior to contact with the catalyst.

In the process of the invention the hydrogen-containing gas:dialkyl 1,4-cyclohexanedicarboxylate molar ratio, one of the driving forces for the hydrogenation and isomerisation reactions, can vary within wide limits, depending upon other process variables such as the feed temperature and feed pressure employed and the activity of the hydrogenation catalyst.

In order to maintain the vaporous feed stream above its dew point at the inlet end of the or each catalyst bed at the operating pressure the hydrogen-containing gas:-dialkyl (e.g. dimethyl) 1,4-cyclohexanedicarboxylate molar ratio is desirably at least about 10:1 up to about 8000:1, preferably in the range of from about 200:1 to about 1000:1. It is not, however, necessary that, when using dimethyl 1,4-cyclohexanedicarboxylate as diester starting material, the vaporous mixture in contact with all parts of the or each catalyst bed should be so far above its dew point as to prevent condensation of a 1,4-cyclohexanedimethanol-rich liquid. (1,4-Cyclohexanedimethanol is less volatile than dimethyl 1,4-cyclohexanedicarboxylate).

Although the process of the invention is operated with the feed stream in the vapour phase, it is convenient to express the feed rate of the dialkyl 1,4-cyclohexanedicarboxylate to the hydrogenation zone of step (e) of the process as a space velocity through the hydrogenation catalyst and to express that space velocity as a liquid hourly space velocity. Hence it is convenient to express the feed rate in terms of the ratio of the liquid feed rate of the hydrogenatable material to the vaporisation zone to the volume of the hydrogenation catalyst. Thus the equivalent liquid hourly space velocity of the hydrogenatable material through the hydrogenation catalyst is preferably from about 0.05 to about 4.0 $h^{-1}$. In other words it is preferred to feed the liquid hydrogenatable material to the vaporisation zone at a rate which is equivalent to, per unit volume of catalyst, from about 0.05 to about 4.0 unit volumes of hydrogenarable material per hour (i.e. about 0.05 to about 4.0 $m^3h^{-1}$ per $m^3$ of catalyst). Even more preferably the liquid hourly space velocity is from about 0.1 $h^{-1}$ to about 1.0 $h^{-1}$.

The Actual Residence Time of the reaction mixture in contact with the hydrogenation catalyst is readily calculated from the feed rate of the dialkyl 1,4-cyclohexanedicarboxylate to the hydrogenation zone, from the hydrogen-containing gas:dimethyl 1,4-cyclohexanedicarboxylate molar ratio, from the volume of catalyst in the hydrogenation zone, and from the temperature and pressure in the hydrogenation zone. If the plant includes two or more hydrogenation zones connected in series or in parallel downstream from the vaporisation zone, then the plant operator can radically alter the effective volume of catalyst by selecting how many zones should be in use at any given time.

The Actual Residence Time needed to produce from a given dialkyl (e.g. dimethyl) 1,4-cyclohexanedicarboxylate feedstock a 1,4-cyclohexanedimethanol product having a desired trans-:cis- isomer ratio is dependent upon a number of factors such as the dialkyl 1,4-cyclohexanedicarboxylate feed rate, the hydrogen-containing gas:dialkyl (e.g. dimethyl) 1,4-cyclohexanedicarboxylate molar ratio, and the catalyst activity. Although the catalyst will tend to decline in activity with passage of time in a commercial plant, the rate of decline, although significant if measured over a matter of months, is relatively slow. Thus it is possible to establish the effects of changing the four most important feed conditions, i.e. feed temperature, the feed pressure, the feed rate, and the hydrogen-containing gas:dimethyl 1,4-cyclohexanedicarboxylate molar ratio, on the trans-:cis- isomer ratio in the 1,4-cyclohexanedimethanol product experimentally over a period of time which is sufficiently short for any change in catalyst activity to be insignificant.

The activity of the catalyst at a reference time, i.e. the Reference Activity (RA), which is conveniently given the arbitrary value 1.0, is readily established either in the laboratory or in an operating plant by measuring the extent of conversion of a dialkyl (e.g. dimethyl) 1,4-cyclohexanedicarboxylate in passage of the feedstock in a vaporous feed stream in admixture with a hydrogen-containing gas under a convenient set of standard operating conditions using a known volume of catalyst. The Actual Activity (AA) of the catalyst, which is conveniently expressed as a decimal fraction of the Reference Activity (RA) (e.g. as 0.89, to take an arbitrary example), at any later time can be determined by re-measuring the extent of conversion of the dialkyl 1,4-cyclohexanedicarboxylate to 1,4-cyclohexanedimethanol using the same operating conditions and catalyst. From such operating data it is possible to develop a body of data to enable the plant operator to determine the Actual Activity of the catalyst under the prevailing operating conditions without having to revert to conditions corresponding to the preselected or standard operating conditions under which the Reference Activity of the catalyst was determined.

As the Actual Activity of the catalyst, determined as described hereinabove, declines during extended operation of the hydrogenation process, it is apparent that the Actual Residence Time (ART) will need to be increased in order to maintain a given Effective Residence Time (ERT) according to the relationship:

$$ART = \frac{ERT \times RA}{AA}.$$

The results of our experimental programme have further shown that, by changing the operating conditions to change the effective residence time, it is possible to change the trans-:cis- isomer ratio in the 1,4cyclohexanedimethanol product to any desired value within a wide range of values, e.g. from about 1:1 to about 3.84:1, when using a dialkyl 1,4-cyclohexanedicarboxylate feedstock that has a trans-:cis-isomer ratio less than about 3.84:1, e.g. a trans-:cis-isomer ratio of from about 0.5:1 to about 0.6:1. If a dialkyl 1,4-cyclohexanedicarboxylate feedstock is used that has a trans-:cis-isomer ratio higher than about 3.84:1, for example if trans-dimethyl cyclohexanedicarboxylate is used as feedstock, then the trans-:cis-isomer ratio in the 1,4-cyclohexanedimethanol produce may be higher than about 3.84:1. A plant operator can utilise the teachings of the invention to maintain a given trans-:cis- isomer ratio in the 1,4-cyclohexanedimethanol product throughout the life of a given catalyst charge despite decline in its activity or to maintain this ratio despite changes in the isomer content of the diester feedstock. It also enables him to change the isomer ratio in the product at will in response to changing product specification requirements.

It will be appreciated that the effective residence time appropriate to produce a desired trans-:cis- isomer ratio in the 1,4-cyclohexanedimethanol product from one particular feedstock, e.g. cis- dimethyl 1,4-cyclohexanedicarboxylate, may not necessarily be the same for a different feedstock, e.g. the trans- diester. Hence it may be necessary to carry out one or more experiments for each new feedstock that is used in order to determine for that feedstock what are the particular combinations of effective residence time and effective operating conditions required to produce a particular trans-:cis- isomer ratio in the product. Such effective operating conditions are typically conditions selected from within the ranges of feed temperature, feed pressure, feed rate and hydrogen-containing gas:dialkyl 1,4-cyclohexanedicarboxylate molar ratio recommended for use in steps (d) and (e) of the process of the invention. Having determined for one feedstock what are appropriate operating conditions for one feedstock having a particular trans-:cis- isomer ratio, then if the new feedstock has only a slightly different isomer ratio it may suffice to carry out only one test or a few tests in order to determine with sufficient accuracy what changes are needed to the operating conditions which were appropriate for the former feedstock to achieve with the new feedstock the desired new effective residence time which will yield the desired isomer ratio. On the other hand, if the new dialkyl 1,4-cyclohexanedicarboxylate feedstock differs very markedly in its trans-:cis- isomer ratio from that of the former feedstock, then a more extensive experimental programme may be necessary to yield the relevant data from which the new effective residence time can be determined.

It is recognised by those skilled in the art that, as catalyst activity declines, the feed temperature and/or the feed pressure may be adjusted so as to improve the rate of hydrogenation of dialkyl 1,4-cyclohexanedicarboxylate. When increasing the feed temperature and/or feed pressure to the hydrogenation zone, it is possible to use the same relationship to control the trans-:cis- isomer ratio in the product 1,4-cyclohexanedimethanol, except that now a different Effective Residence Time (ERT) will be required. This new Effective Residence Time (ERT) can easily be determined by monitoring the product trans-:cis-isomer content and adjusting the Actual Residence Time (ART) as necessary in order to achieve the desired trans-:cis-isomer ratio in the product 1,4-cyclohexanedimethanol.

As the activity of the catalyst changes with time, it is possible to alter the feed rate, without altering the temperature, in order to change the effective residence time and so maintain the molar conversion of dialkyl dimethyl) 1,4-cyclohexanedicarboxylate substantially at a constant value. In this way changes in the feed rate can be used to keep the trans-:cis- isomer ratio of the product 1,4-cyclohexanedimethanol substantially at a desired constant value.

A further option is to increase the feed temperature to the hydrogenation zone while reducing the hydrogen-containing gas:dialkyl 1,4-cyclohexanedicarboxylate molar ratio in order to maintain a constant approach to the dew point of the feed stream. Thus, for example, it is possible to increase the feed temperature of the feed stream, a step which would increase the amount by which the temperature exceeds the dew point of the feed stream if the other operating conditions were not changed, and simultaneously to reduce the hydrogen-containing gas:dialkyl 1,4-cyclohexanedicarboxylate molar ratio, a step which would otherwise decrease the amount by which the dew point of the feed stream exceeds its dew point if the other operating conditions were not changed, so as to leave the difference between the dew point and the feed temperature effectively the same, i.e. so as to operate at a substantially constant approach to the dew point. One skilled in the art will recognise that, when changing feed temperature to the hydrogenation zone, a new effective residence time will be required in order to maintain the target trans-:cis-isomer ratio in the 1,4-cyclohexanedimethanol product.

With passage of time the activity of the catalyst tends to decline. However, it has been found in the course of our experimental programme that it is possible to reactivate the catalyst by treating the partially deactivated hydrogenation catalyst with a flow of a hydrogen-containing gas, which is substantially free from dialkyl (e.g. dimethyl) 1,4-cyclohexanedicarboxylate, under appropriate temperature and pressure conditions. If such a procedure is used in the course of a particular production campaign, then the Actual Activity (AA) may be increased again and it may be necessary after such reactivation to increase the feed rate and/or to reduce the residence time from the corresponding values in use preceding the reactivation procedure in order to re-achieve the effective residence time and the desired extent of conversion of dimethyl 1,4-cyclohexanedicarboxylate required to achieve the desired trans-:cis- isomer ratio in the 1,4-cyclohexanedimethanol product.

In a particularly preferred process the dialkyl 1,4-cyclohexanedicarboxylate is a cis-rich isomer mixture and the operating conditions are selected so as to produce a 1,4-cyclohexanedimethanol product in which the trans-:cis- isomer ratio is in the range of from about 2:1 up to about 3.84:1, and is more preferably at least about 2.6:1 up to about 3.84:1. The process of the invention thus readily permits the preparation in a single step from such a cis-rich feedstock of a 1,4-cyclohexanedimethanol product in which the trans-:cis- isomer ratio is in excess of about 2:1 up to about 3.84:1, for example from about 2.6:1 to about 2.7:1. It is preferred that this ratio is at least about 2.6:1. The invention permits production in a single step of a 1,4-cyclohexanedimethanol product with a trans-:cis- isomer ratio of from about 3.1:1 up to about 3.84:1, e.g. about 3.2:1 up to about 3.7:1. Higher trans-:cis- isomer ratios can be achieved in the 1,4-cyclohexanedimethanol product by starting from trans-dimethyl 1,4-cyclohexanedicarboxylate.

It is surprising that the vapour phase feed conditions used in the process of the invention can generate from a cis-rich diester feedstock a 1,4-cyclohexanedimethanol product mixture whose trans-:cis-isomer ratio is in excess of the ratio that is the normal reported equilibrium ratio under liquid phase conditions. Thus, although the normal trans-:cis- isomer equilibrium ratio in the 1,4-cyclohexanedimethanol product from a cis-rich diester feedstock, under liquid phase conditions, is reported to be, under favourable conditions, as high as about 3:1, the present invention, which operates with the feed ester (e.g. dimethyl 1,4-cyclohexanedicarboxylate) always in the vapour phase, enables production from a dialkyl 1,4-cyclohexanedicarboxylate feedstock with a trans-:cis- isomer ratio less than about 1:1 of 1,4-cyclohexanedimethanol with a trans-:cis-isomer ratio as high as 3.84:1.

In the prior art it is made clear that the hydrogenation of dimethyl 1,4-cyclohexanedicarboxylate (dimethyl hexahydroterephthalate) is liable to give significant quantities of by-products. Thus GB-A-988316 acknowledges the problem caused by formation of unwanted by-products, such as 1-methyl-4-hydroxymethylcyclohexane. It is surprising to find that the process of the invention can be operated so that, despite the presence of a very large excess of hydrogen and the use of a very large partial pressure of hydrogen compared to the relatively low vapour pressure of dimethyl 1,4-cyclohexanedicarboxylate, the reaction proceeds rapidly with a very high conversion of dimethyl 1,4-cyclohexanedicarboxylate to the desired product, i.e. 1,4-cyclohexanedimethanol, but yet with a very high selectivity to that product and therefore with a very low yield of by-products. Thus under favourable conditions the conversion of dimethyl 1,4-cyclohexanedicarboxylate to 1,4-cyclohexanedimethanol can be as high as 98 mole % or higher with a selectivity to 1,4- cyclohexanedimethanol of greater than 96 mole %. In addition it surprising to find that it is possible, under suitable reaction conditions, to convert a starting ester (e.g. dimethyl 1,4-cyclohexanedicarboxylate) that has a trans-:cis- isomer ratio less than 1:1 in a single step to a cyclohexanedimethanol product with a trans-:cis- isomer ratio that is greater than 1:1 and normally in the range of from about 2.6:1 up to as high as about 3.84:1, a value that is much higher than the highest equilibrium trans-:cis- isomer ratio that is disclosed in the prior art. It is further surprising to find that this conversion can be accomplished at relatively low operating temperatures and pressures.

In a commercial plant it may be preferred to employ at least two hydrogenation zones, each containing a charge of a heterogeneous ester hydrogenation catalyst, connected in parallel. Each of these zones is capable of independent isolation from the supply of vaporous feedstock mixture. Hence an isolated zone may be subjected to conditions substantially different from those prevailing in the remaining zone or zones, for example, whereunder the catalyst charge therein may be reactivated or replaced whilst the process of the invention is continued in the remaining zone or zones. This arrangement also permits operation under the conditions taught in WO-A-91/01961. In this case two hydrogenation reactors connected in parallel are used. In a first phase of operation with a fresh charge of catalyst one only of the reactors is used, the other one being in standby mode with the catalyst bathed in hydrogen. After a period of operation over which the catalyst activity may decline somewhat the second reactor is used, whilst the first one is placed in standby condition. After a further period of operation both reactors are used in parallel until the time comes to replace the entire catalyst charge.

It is also possible to use two or more hydrogenation zones connected in series and to bypass one or more of these if it is desirable to reduce the quantity of catalyst on line at any given time.

The granular catalyst used in the process of the invention may be any catalyst capable of catalysing hydrogenation or hydrogenolysis of an ester to the corresponding alcohol or mixture of alcohols. It may be formed into any suitable shape, e.g. pellets, rings or saddles.

Typical ester hydrogenation catalysts include copper-containing catalysts and Group VIII metal-containing catalysts. Examples of suitable copper-containing catalysts include copper-on-alumina catalysts, reduced copper oxide/zinc oxide catalysts, with or without a promoter, manganese promoted copper catalysts, and reduced copper chromite catalysts, with or without a promoter, while suitable Group VIII metal-containing catalysts include platinum catalysts and palladium catalysts. Suitable copper oxide/zinc oxide catalyst precursors include CuO/ZnO mixtures wherein the Cu:Zn weight ratio ranges from about 0.4:1 to about 2:1. An example is the catalyst precursor bearing the designation DRD 92/71. Promoted copper oxide/zinc oxide precursors include CuO/ZnO mixtures wherein the Cu:Zn weight ratio ranges from about 0.4:1 to about 2:1 which are promoted with from about 0.1% by weight up to about 15% by weight of barium, manganese or a mixture of barium and manganese. Such promoted CuO/ZnO mixtures include the Mn-promoted CuO/ZnO precursor available under the designation DRD 92/92. Suitable copper chromite catalyst precursors include those wherein the Cu:Cr weight ratio ranges from about 0.1:1 to about 4:1, preferably from about 0.5:1 to about 4:1. Catalyst precursors of this type are the precursors available under the designation DRD 89/21 or under the designation PG 85/1. Promoted copper chromite precursors include copper chromite precursors wherein the Cu:Cr weight ratio ranges from about 0.1:1 to about 4:1, preferably from about 0.5:1 to about 4:1, which are promoted with from about 0.1% by weight up to about 15% by weight of barium, manganese or a mixture of barium and manganese. Manganese promoted copper catalyst precursors typically have a Cu:Mn weight ratio of from about 2:1 to about 10:1 and can include an alumina support, in which case the Cu:Al weight ratio is typically from about 2:1 to about 4:1. An example is the catalyst precursor DRD 92/89.

All of the above mentioned catalysts available under the general designations DRD or PG can be obtained from Davy Research and Development Limited, P.O. Box 37, Bowesfield Lane, Stockton-on-Tees, Cleveland TS18 3HA, England.

Other catalysts which can be considered for use include Pd/ZnO catalysts of the type mentioned by P.S. Wehner and B.L. Gustafson in Journal of Catalysis 136, 420– 426 (1992), supported palladium/zinc catalysts of the type disclosed in U.S. Pat. No. 4,837,368 and U.S. Pat. No. 5,185,476, and chemically mixed copper-titanium oxides of the type disclosed in U.S. Pat. No. 4,929,777.

Further catalysts of interest for use in the process of the invention include the rhodium/tin catalysts reported in A. El Mansour, J.P. Candy, J. P. Bournonville, O. A. Ferrehi, and J. M Basset, Angew. Chem. 101, 360 (1989).

Any recognised supporting medium may be used to provide physical support for the catalyst used in the process of the invention. This support can be provided by materials such as zinc oxide, alumina, silica, alumina-silica, silicon carbide, zirconia, titania, carbon, a zeolite, or any suitable combination thereof.

The catalysts that are particularly preferred for use in the process of the invention are the reduced forms of the copper chromite, promoted copper chromite, and manganese promoted copper catalyst precursors described above.

The or each hydrogenation zone may comprise a shell-and-tube reactor which may be operated under isothermal, or near isothermal, conditions with the catalyst in the tubes and the coolant in the shell or vice versa. Usually, however, it will be preferred to use adiabatic reactors since these are cheaper to construct and install than shell-and-tube reactors. Such an adiabatic reactor may contain a single charge of a hydrogenation catalyst or may contain two or more beds of catalyst, or beds of different hydrogenation catalysts. If desired, external or internal inter-bed heat exchangers may be provided in order to adjust the inlet temperature to one or more beds of catalyst downstream from the inlet to the adiabatic hydrogenation reactor.

In an alternative procedure the plant includes at least two hydrogenation zones, each containing a charge of granular hydrogenation catalyst, and the vaporous feed stream is supplied to at least one of the hydrogenation zones, in a first phase of operation, while at least one other hydrogenation zone is supplied with a stream of hydrogen-containing gas thereby to reactivate the charge of hydrogenation catalyst therein. In a second phase of operation the at least one other hydrogenation zone is supplied with the vaporous feed stream while the at least one hydrogenation zone is supplied with a stream of hydrogen-containing gas thereby to reactivate the charge of hydrogenation catalyst therein.

In this procedure the or each hydrogenation zone that is not on line is supplied with a stream of hydrogen-containing gas thereby to reactivate the catalyst charge. Normally it will be preferred to carry out this reactivation at elevated temperature, typically at a temperature of about 100° C. or more up to about 350° C. In this reactivation step the inlet temperature to the respective hydrogenation zone or zones may be lower than, substantially equal to, or higher than, e.g. about 10° C. to about 50° C. higher than, the inlet temperature of the vaporous feed stream to the on line hydrogenation zone or zones. The stream of hydrogen-containing gas used in such a reactivation step may comprise a hot stream of recycle and make-up gas.

In one form of this alternative procedure is recovered from the zone or zones undergoing reactivation of the catalyst a stream of hydrogen-containing gas which is admixed with a vaporous hydrogen-containing stream of the dialkyl cyclohexanedicarboxylate to form the vaporous feed stream to the on line zone or zones. In another form there is recovered from the zone or zones whose catalyst is undergoing reactivation a stream of hydrogen-containing gas which is admixed with the reaction product stream from the on line zone or zones. In a still further form of this alternative procedure there is recovered from the zone or zones undergoing catalyst reactivation a stream of hydrogen-containing gas which is used to vaporise the dialkyl cyclohexanedicarboxylate to form a vaporous hydrogen-containing stream of the dialkyl cyclohexanedicarboxylate. It is further convenient to form the vaporous feed stream to the on line zone or zones by admixing hot recycle gas with a vaporous hydrogen-containing stream of dialkyl cyclohexanedicarboxylate. The direction of flow of the stream of hydrogen-containing gas through the or each hydrogenation zone in which catalyst reactivation is occurring may be the same as, or opposite to, the direction of flow of the vaporous feed stream through that zone when it is on line.

In summary, the process of the invention can be controlled to produce a desired trans-:cis- ratio in the cyclohexanedimethanol product. This control is achievable due to the surprising discovery that, in the process of the invention, the trans-:cis- isomer ratio in the 1,4-cyclohexanedimethanol product is a function of the extent of dimethyl 1,4-cyclohexanedicarboxylate conversion effected in the hydrogenation zone. The extent of conversion of dimethyl 1,4-cyclohexanedicarboxylate in turn dependent upon the effective residence time, which is, in turn, a function of the activity of the catalyst, of the volume of catalyst, of the feed temperature, of the temperature profile through the catalyst bed or beds, of the feed pressure, of the hydrogen-containing gas:dimethyl 1,4-cyclohexanedicarboxylate ratio, and of the feed rate of the reaction mixture through the catalyst, under the vapour phase hydrogenation conditions used. Hence, by controlling the amount of conversion of dimethyl 1,4-cyclohexanedicarboxylate that is occurring in the hydrogenation zone as the catalyst ages, or following catalyst reactivation, the plant operator can exercise control over the trans-:cis- ratio of the 1,4-cyclohexanedimethanol product.

DETAILED DESCRIPTION OF THE PREFERRED EMBODIMENTS

Figure 1:
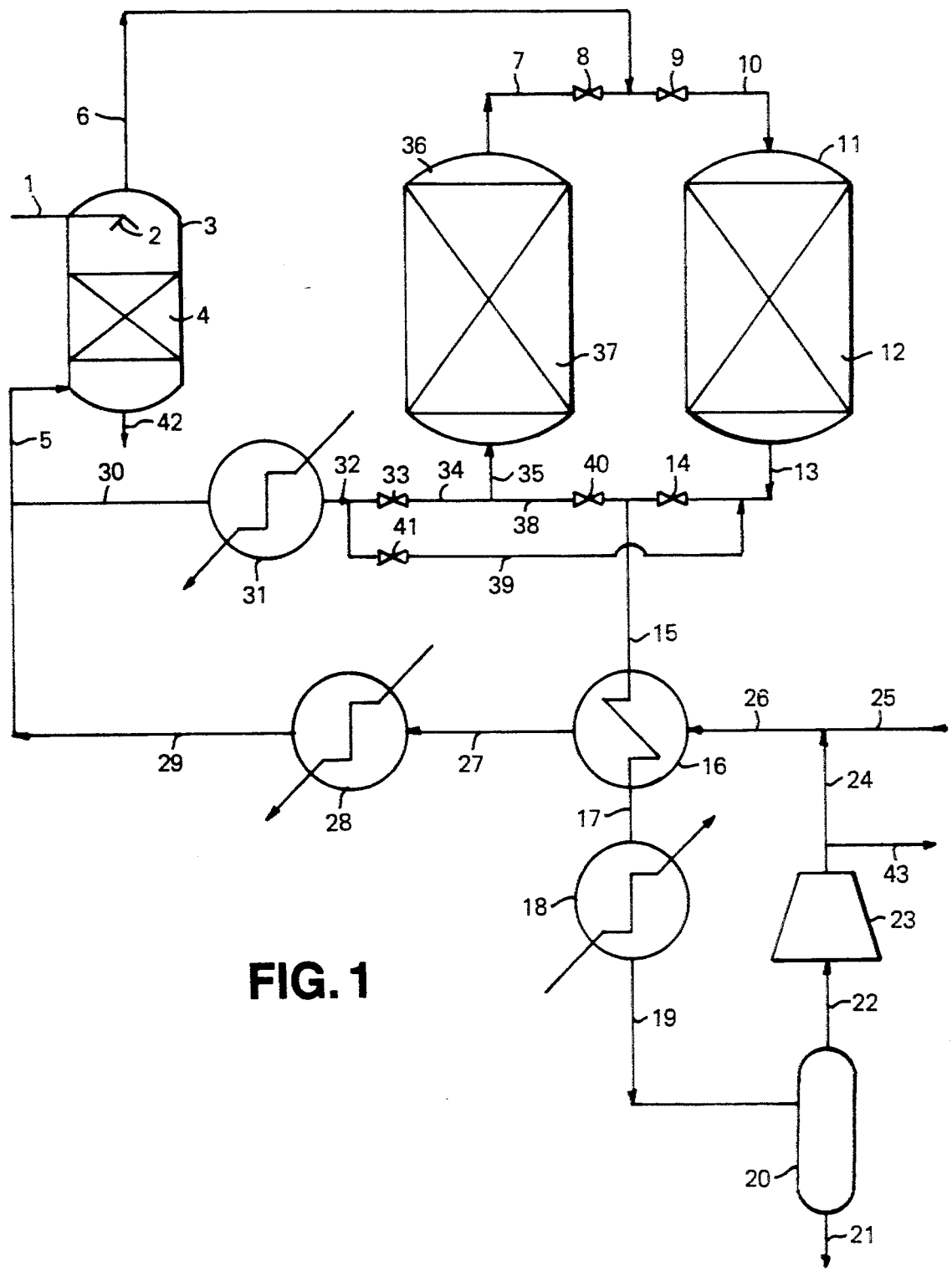
FIG. 1 is a simplified flow diagram of a plant for production of 1,4-cyclohexanedimethanol in two hydrogenation reactors connected in parallel by hydrogenation of dimethyl 1,4-cyclohexanedicarboxylate.

It will be understood by those skilled in the art that FIG. 1 of the drawings is diagrammatic and that further items of equipment such as temperature and pressure sensors, pressure relief valves, control valves, level controllers and the like would additionally be required in a commercial plant. The provision of such ancillary items of equipment forms no part of the present invention and would be in accordance with conventional chemical engineering practice. Moreover it is not intended that the scope of the invention should be limited in any way by the precise methods of heating, vaporising and condensing various process streams or by the arrangement of heaters, heat exchangers, vaporising or condensing apparatus provided therefor. Any suitable arrangement of equipment other than that depicted in FIG. 1 which fulfils the requirements of the invention may be used in place of the illustrated equipment in accordance with conventional chemical engineering techniques.

Referring to FIG. 1 of the drawings, a technical grade of dimethyl 1,4-cyclohexanedicarboxylate is supplied in line 1, in a first phase of operation, to a vaporiser nozzle 2 located in an upper part of a vaporiser vessel 3 above a bed of packing 4. A stream of hot hydrogen-containing gas is supplied to the bottom of vaporiser vessel 3 in line 5. A saturated vaporous mixture comprising dimethyl 1,4-cyclohexanedicarboxylate is recovered in line 6 from the top of vaporiser vessel 3. The resulting vaporous mixture is mixed with further hot hydrogen-containing gas from line 7 under the control of valve 8. The combined stream which now has a hydrogen:dimethyl 1,4-cyclohexanedicarboxylate molar ratio of about 400:1 and is at a pressure of about 905 psia (about 62.40 bar) and at a temperature of about 220° C., is fed by way of valve 9 and line 10 to a hydrogenation reactor 11 which contains a bed of a pelleted heterogeneous hydrogenation catalyst 12, such as reduced copper chromite or the chromium-free catalyst designated DRD92/89. The hydrogenation reaction product mixture exits reactor 11 via line 13 and passes through valve 14 to enter line 15. The hydrogenation reaction product mixture in line 15 is cooled in heat interchanger 16 and the resulting partially condensed mixture passes on in line 17 through cooler 18 in which it is further cooled. The resulting mixture of gas and condensate flows on in line 19 to a gas-liquid separator 20 from which a mixture of methanol and crude 1,4-cyclohexanedimethanol is recovered in line 21. The uncondensed gaseous mixture in line 22 comprises unreacted hydrogen together with inert gases and methanol vapour and is compressed by means of compressor 23 to give a compressed gas stream in line 24.

The compressed recycled gas in line 24 is combined with make-up hydrogen-containing gas from line 25. The combined mixture in line 26 is heated by passage through heat exchanger 16 and flows on in line 27 to heater 28 in which its temperature is raised further to a suitable temperature for effecting vaporisation of the dimethyl 1,4-cyclohexanedicarboxylate feed. The resulting hot gas in line 29 is then divided into two streams, one being the stream in line 5 and the other being a stream in line 30. This latter stream is heated further in heater 31 to a temperature of about 235° C. and passes on by way of line 32, valve 33 and lines 34 and 35 to the bottom end of a second hydrogenation reactor 36 which, in this first phase of operation, is in reactivation mode. Reactor 36 contains a charge of hydrogenation catalyst 37. The hot gas exiting the top of reactor 36 in line 7 is admixed, as already described above, with the saturated vaporous mixture in line 6 to increase the hydrogen:dimethyl 1,4-cyclohexanedicarboxylate molar ratio therein and to raise its temperature above its dew point, e.g. at least 5° C. to 10° C. above its dew point.

The plant also includes lines 38 and 39 and valves 40 and 41 both of which are closed in this phase of operation. Line 42 indicates a line by means of which a stream containing any "heavies" collecting in the bottom of vaporiser vessel 3 can be drawn off. Reference numeral 43 indicates a purge gas line through which a purge gas stream can be taken in order to limit the build up of inert gases in the circulating gas. Such inert gases may enter the plant in the make up gas stream in line 25.

With passage of time the activity of the catalyst charge 12 will have declined somewhat. The plant operator can maintain the desired trans-:cis- isomer ratio in the 1,4-cyclohexanedimethanol product by monitoring this ratio in the exit stream from the on line hydrogenation zone. By altering the reaction conditions, for example, by reducing the space velocity through the hydrogenation catalyst, the effective residence time can be maintained substantially constant and thus the extent of conversion of dimethyl 1,4-cyclohexanedicarboxylate can be maintained at a substantially constant value. In this way it is possible to maintain the trans-:cis- isomer ratio in the product at the desired value, for example, a value in the range of from about 2.6:1 to about 2.7:1 or higher, up to about 3.84:1 (e.g. from about 3.1:1 up to about 3.7:1).

After a period of operation the activity of the catalyst charge 12 will have declined to a point at which reactivation may be desirable. Although the reasons for catalyst deactivation have not been clarified, it can be postulated that a possible cause of this loss of catalyst activity is the formation of traces of involatile polyesters on the catalyst surface due to ester exchange reactions between, for example, dimethyl 1,4-cyclohexanedicarboxylate, on the one hand, and 1,4-cyclohexanedimethanol, or methyl 4-hydroxymethylcyclohexanecarboxylate, which can be postulated to be an intermediate product of the hydrogenation reaction, or hydroxymethylcyclohexylmethyl 1,4-cyclohexanedicarboxylate, which is the ester interchange product between dimethyl 1,4-cyclohexanedicarboxylate and 1,4-cyclohexanedimethanol, on the other hand. The resulting di- or trimeric materials can then undergo further reaction with components of the vaporous mixture to cause these oligomeric chains to grow. Polyethers and mixed polyetherpolyesters can also be formed.

Such polymeric byproducts on the catalyst surface are susceptible to hydrogenation. Hence reactivation of the catalyst by treatment with a hot hydrogen-containing gas is possible. It has further been shown in the course of experimental work to investigate the hydrogenation of dimethyl 1,4-cyclohexanedicarboxylate which forms the background to the present invention that, for whatever reason, the passage of a hot stream of hydrogen-containing gas over partially deactivated catalyst has a beneficial effect in at least partially restoring the activity of the catalyst.

Accordingly in a second phase of operation valve 33 is shut and valve 41 is opened, while valve 14 is closed and valve 40 is opened. In this way hydrogenation reactor 36 with its fresh or reactivated catalyst charge 37 is brought on line, whilst reactor 11 goes into reactivation mode and its partially deactivated charge of catalyst 12 is reactivated. In this second mode of operation the saturated vaporous mixture in line 6 is mixed with hot hydrogen-containing gas from line 10 to form a vaporous feed mixture which flows in line 7 through reactor 36 and its catalyst charge 37. The resulting reaction mixture passes by way of lines 35 and 38 through valve 40 to line 15. The hot hydrogen-containing gas from line 32 passes through valve 41 to line 39 and then through line 13 to the bottom of hydrogenation reactor 11.

In this second phase of operation the plant operator can also monitor the trans-:cis- isomer ratio in the 1,4-cyclohexanedimethanol product of the exit stream from the on line hydrogenation zone and can adjust the conditions, as before, to maintain the effective residence time of the reaction mixture in the hydrogenation zone substantially constant and hence maintain the trans-:cis-1,4-cyclohexanedimethanol ratio at the desired level.

When the catalyst charge 37 has become deactivated to some extent the valves 14, 33, 40 and 41 can be readjusted to switch the flows through hydrogenation reactors 11 and 36 back to those of the first phase of operation.

The above described steps can be repeated as often as may be expedient, bringing the reactors 11 and 36 on line in turn until the reactivation procedure no longer results in the desired increase in catalyst activity or until the plant has to be shut down for maintenance or other reasons, whereupon the catalyst charges 12 and 37 can be discharged and replaced by fresh charges of catalyst or catalyst precursor.

The make-up gas in line 25 can be a mixture of hydrogen, optional minor amounts of components such as CO and $CO_2$, and inert gases, such as argon, nitrogen, or methane, containing at least about 70 mole % of hydrogen. Preferably the make-up gas contains at least 90 mole %, and even more preferably at least 97 mole %, of hydrogen. The make-up gas can be produced in any convenient manner, e.g. by partial oxidation or steam reforming of natural gas followed by the water gas shift reaction, and $CO_2$ absorption, followed possibly by methanation of at least some of any residual traces of carbon oxides. Pressure swing absorption can be used if a high purity hydrogen makeup gas is desired.

At start up of the plant the reactors 11 and 36 are each charged with a charge of a heterogeneous hydrogenation catalyst precursor, such as a copper chromite catalyst precursor. Preferably, however, the reactors 11 and 36 are charged with a chromium-free hydrogenation catalyst, such as DRD92/89. The catalyst precursor is then reduced carefully following the catalyst supplier's instructions. If the process of EP-A-0301853 is used to reduce a copper chromite precursor, then both beds of catalyst 12 and 37 can be reduced simultaneously. In other cases it may be expedient to reduce the beds 12 and 37 separately. After pre-reduction of the catalyst precursor hot hydrogen-containing gas is circulated through the plant. When the appropriate feed temperatures to vaporiser vessel 3 and to reactor 11 have been achieved the flow of dimethyl 1,4-cyclohexanedicarboxylate in line 1 is commenced to bring the plant on line in the first phase of operation.

Figure 3:
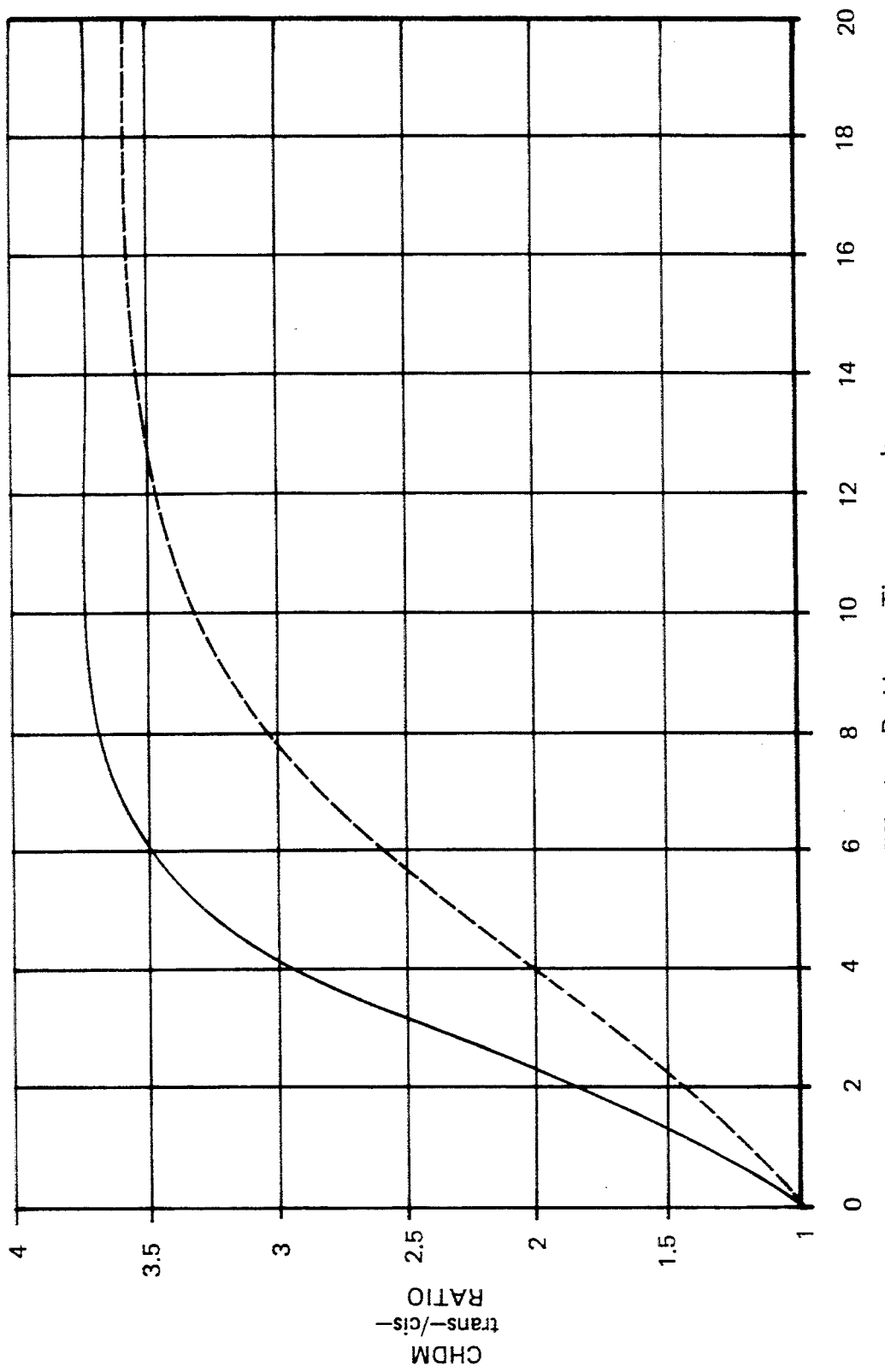
FIG. 3 is a graph showing the relationship between the effective residence time and the trans-:cis- ratio of the resulting 1,4-cyclohexanedimethanol product derived from the experimental results for two combinations of feed temperatures and feed pressures.

The invention is further described with reference to the following Examples. The compositions of catalysts A and B used in the Examples are listed in Table I. The oxygen content of the catalyst has been excluded from the analysis in each case. The Examples, taken together with the information summarised in FIG. 3, provide the man skilled in the art with teaching as to the reaction conditions that he needs to select at any particular moment in the production campaign in response to changes in catalyst activity.

TABLE I

| Catalyst | Composition wt % | | | | | | Surface area m$^2$/g | Density g/cm$^3$ | Pore volume mm$^3$/g |
| | Cu | Cr | Zn | Mn | Ba | Al | | | |
| --- | --- | --- | --- | --- | --- | --- | --- | --- | --- |
| A DRD 89/21 | 57.6 | 19.0 | <0.01 | 0.09 | <0.01 | <0.01 | 28 | 1.420 | 200 |
| B DRD 92/89 | 41.1 | 0.26 | <0.01 | 6.4 | <0.01 | 20.4 | 47.1 | 1.452 | 211 |

EXAMPLE 1

Figure 2:
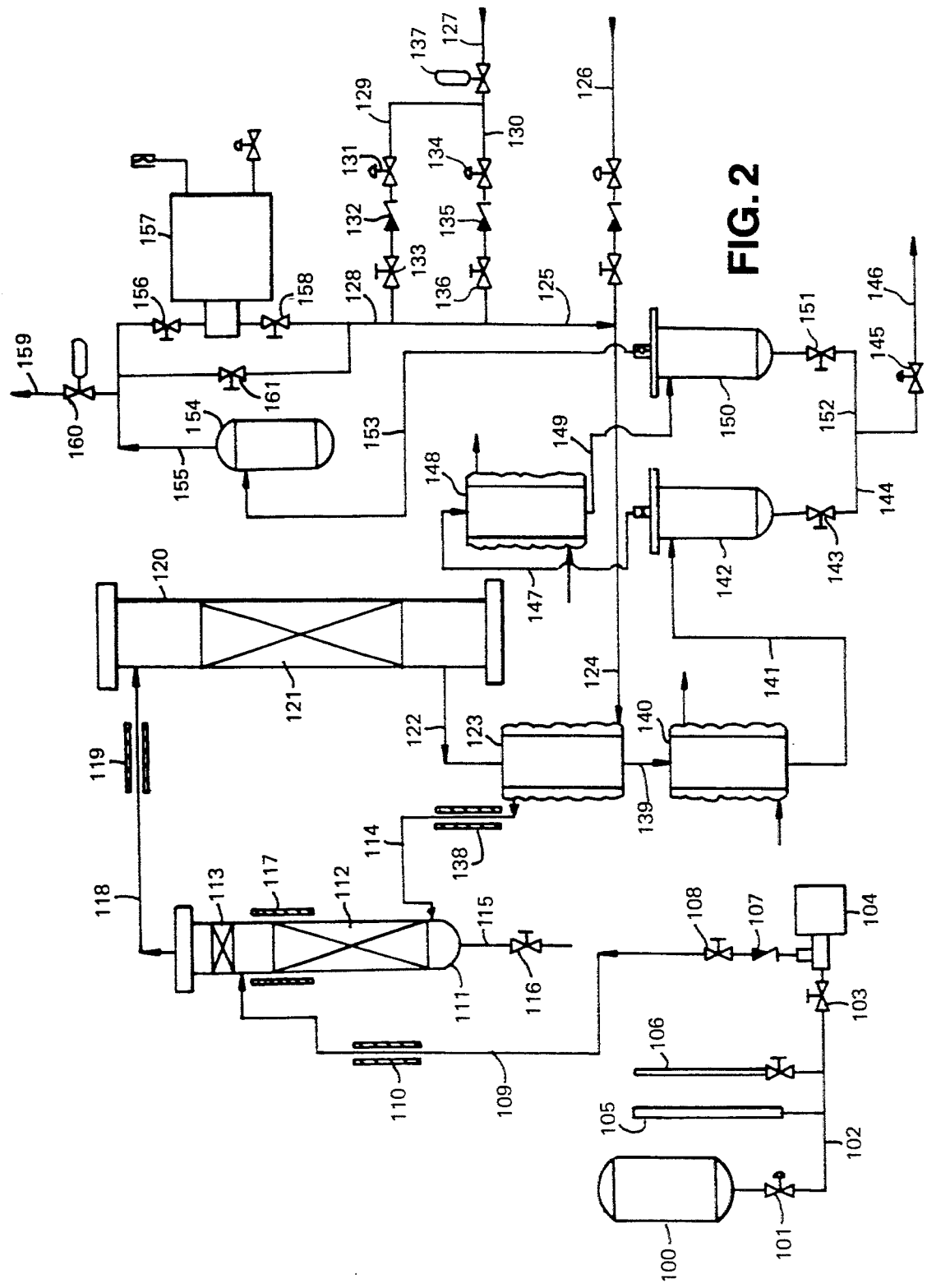
FIG. 2 is a simplified flow diagram of an experimental apparatus for production of 1,4-cyclohexanedimethanol in a single hydrogenation zone by hydrogenation of dimethyl 1,4-cyclohexanedicarboxylate.

The hydrogenation of a technical grade of dimethyl 1,4-cyclohexanedicarboxylate was investigated using the experimental apparatus illustrated in FIG. 2.

The composition of the technical garde used was: 34.47 wt % trans-dimethyl 1,4-cyclohexanedicarboxylate, 62.61 wt % cis-dimethyl 1,4-cyclohexanedicarboxylate, 1.50 wt % methyl hydrogen 1,4-cyclohexanedicarboxylate of formula

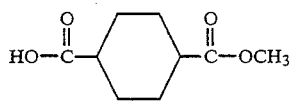

and 0.05 wt % water, with the balance being impurities.

In a commercial plant, hydrogen gas is separated from the hydrogenation product and is advantageously recycled through the hydrogenation zone. The hydrogen recycle stream will contain a quantity of methanol vapour produced by the hydrogenation of dimethyl 1,4-cyclohexanedicarboxylate. Hence, the vaporous mixture supplied to the hydrogenation zone in a commercial plant will generally contain methanol in addition to hydrogen and an unsaturated organic compound. In order that the experimental rig described hereinbelow should accurately predict the likely results obtained during commercial operation, the liquid feed supplied to the vaporiser was supplemented by a quantity of liquid methanol corresponding to the quantity of methanol which would be contained in the recycle hydrogen stream in a commercial plant. Although hydrogen is recycled in the experimental rig described hereinbelow, the quantity of methanol contained within the recycle hydrogen stream is proportionately less than would be contained in a corresponding commercial recycle stream. This difference arises because the recycle gas in the experimental rig is cooled substantially below the temperature to which it would be desirably cooled in a commercial plant. More methanol is therefore "knocked out" of the experimental recycle hydrogen stream. This discrepancy between the experimental rig and a commercial plant is necessitated by the delicacy of the equipment, particularly the analytical equipment, used in the experimental rig. In this Example and in all succeeding Examples, methanol is added to the experimental liquid feed in a quantity which is substantially equal to the proportionate quantity of methanol which would be present in the experimental recycle stream if the rig were operated under commercial conditions minus the quantity of methanol actually present in the experimental recycle hydrogen stream. In the Examples, all parameters such as conversion rates and hourly space velocities are calculated on a methanol free basis.

The experimental apparatus is illustrated in FIG. 2. An approximately 70 wt % solution of the technical grade of dimethyl 1,4-cyclohexanedicarboxylate in methanol is fed from reservoir 100 by way of valve 101, line 102 and valve 103 to liquid feed pump 104. Burette 105 provides a buffer supply whilst burette 106 is fitted with a liquid level controller (not shown) that controls valve 101 so as to ensure that liquid feed is supplied from reservoir 100 to liquid feed pump 104 at a constant head. The liquid feed is pumped through non-return valve 107 and isolation valve 108 into line 109, which can be heated by electrical heating tape 110, before the heated liquid enters the upper part of an insulated vaporiser vessel 111 above a bed of 6 mm × 6 mm glass rings 112. A stainless steel demister pad 113 is fitted at the top end of the vaporiser vessel 111. A stream of hot hydrogen-containing gas is supplied to the bottom of vaporiser 111 in line 114. A liquid drain line 115 fitted with a drain valve 116 enables withdrawal of any unvaporised liquid feed material (e.g. "heavies") from the base of the vaporiser vessel 111. The vaporisation of the liquid feed supplied to the vaporiser vessel 111 is assisted by heating tape 117. A saturated vaporous mixture comprising dimethyl 1,4-cyclohexanedicarboxylate and hydrogen is recovered in line 118 from the top of vaporiser vessel 111. The vaporous mixture is heated by heating tape 119 in order to raise its temperature above the dew point of the mixture prior to entering the top end of hydrogenation reactor 120 which contains a bed of 200 ml (321.1 g) of a pelleted copper chromite hydrogenation catalyst 121. The catalyst was catalyst A of Table I. Glass rings are packed in reactor 120 above and below the catalyst bed 121. The vaporous mixture passes downward through catalyst bed 121 where conversion of dimethyl 1,4-cyclohexanedicarboxylate to 1,4-cyclohexanedimethanol occurs under adiabatic conditions. Adiabaticity is maintained by electrical heating tapes (not shown) within insulating material around reactor 120 under the control of appropriately positioned thermocouples (not shown). The overall reaction is mildly exothermic with a general increase in catalyst bed temperature of approximately 1° to 2° C. The hydrogenation product mixture exits the hydrogenation reactor 120 in line 122 and is passed through heat exchanger 123 which simultaneously cools the hydrogenation product mixture and heats a supply of hydrogen-containing gas from line 124. Condensation of the bulk of the 1,4-cyclohexanedimethanol in line 122 occurs in heat exchanger 123. The gas in line 124 comprises hydrogen-containing gas from line 125 and, optionally, an inert gas or a mixture of inert gases such as nitrogen, argon or methane supplied in line 126. The gas in line 125 comprises make-up hydrogen supplied in line 127 and recycle hydrogen supplied in line 128. Make-up hydrogen in line 127 may be supplied to line 125 in either or both of two streams in lines 129 and 130 via a system of pressure controllers 131 to 136 and a mass flow controller 137 from high purity hydrogen cylinders (not shown).

The heated hydrogen-containing gas from heat exchanger 123 passes on in line 114 and is heated further by electrical heating tape 138 for supply to the vaporiser vessel 111.

The cooled hydrogenation product from heat exchanger 123 passes on through line 139 to be cooled further in cooler 140 to a temperature near ambient temperature. The liquid/vapour mixture from cooler 140 passes on in line 141 to a first knockout pot 142 where liquid hydrogenation product is collected for eventual supply by means of valve 143, line 144 and control valve 145 to product line 146. A vaporous mixture comprising hydrogen and uncondensed methanol exits the top of knockout pot 142 in line 147 and is further cooled to a temperature of 10° C. in cooler 148. The further cooled liquid/vapour mixture from cooler 148 is supplied via line 149 to a second knockout pot 150 wherein condensed methanol is collected for eventual supply through valve 151 and line 152 to product line 146. The gas and uncondensed materials from knockout pot 150 are supplied via line 153 through suction pot 154 into line 155 and then through valve 156 to gas recycle compressor 157. Gas is recycled through valve 158 lines 128, 125, 124 and 114 to vaporiser 111. In order to control the concentration of inert gases, such as nitrogen, in the circulating gas a purge gas stream may be bled from the system in line 159 under the control of valve 160.

Reference numeral 161 indicates a bypass valve.

At start up of the apparatus the charge of catalyst was placed in reactor 120 which was then purged with nitrogen. The catalyst charge was then reduced according to the teachings of EP-A-0301853.

Technical grade dimethyl 1,4-cyclohexanedicarboxylate, appropriately diluted with methanol, was then pumped to the vaporiser 111 at a rate of 86 ml/h corresponding to a liquid hourly space velocity of 0.43 $h^{-1}$. The $H_2$:dimethyl 1,4-cyclohexanedicarboxylate mole ratio in the vaporous mixture in line 118 was 338:1. The reactor 120 was maintained at a temperature of 230° C. and a pressure of 901 psia (62.12 bar). The hydrogenation zone was therefore operated under conditions which prevented the condensation of both dimethyl 1,4-cyclohexanedicarboxylate and the less volatile 1,4-cyclohexanedimethanol product. The temperature throughout the hydrogenation zone was above the dew point at the operating pressure.

The liquid in line 146 was analysed periodically by capillary gas chromatography using a 15 m long, 0.32 mm internal diameter fused silica column coated internally with a 0.25 μm film of DB wax, a helium flow rate of 2 ml/minute with a gas feed split ratio of 100:1 and a flame ionisation detector. The instrument was fitted with a chart recorder having a peak integrator and was calibrated using a commercially available sample of dimethyl 1,4-cyclohexanedicarboxylate of known composition. The exit gas was also sampled and analysed by gas chromatography using the same technique. The identities of the peaks were confirmed by comparison of the retention times observed with those of authentic specimens of the materials in question and by mass spectroscopy. Included amongst the compounds detected in the reaction mixture were 1,4-cyclohexanedimethanol, dimethyl 1,4-cyclohexanedicarboxylate, 4-methoxymethyl cyclohexanemethanol, di-(4-methoxymethylcyclohexylmethyl) ether, and methanol. After making due allowance for the methanol present in the feed solution of dimethyl 1,4-cyclohexanedicarboxylate from reservoir 100, 2 moles of methanol were detected for every 1 mole of dimethyl 1,4-cyclohexanedicarboxylate converted in accordance with the stoichiometry of the hydrogenation reaction. The results are listed in Table II below, together with the results from the succeeding Examples 2 to 8. The actual activity of the catalyst is based upon a figure of 1.0 for the reference activity of the freshly reduced catalyst as measured under standard operating conditions at the start of the run. In Example 1 the actual activity of the catalyst was determined to be 0.68 because the percentage of unconverted dimethyl 1,4-cyclohexanedicarboxylate under standard operating conditions was 1.47 times the percentage of unconverted dimethyl 1,4-cyclohexanedicarboxylate under those standard operating conditions when using fresh catalyst. Hence the actual activity, compared to the reference activity of the fresh catalyst of 1.0 was 1/1.47, i.e. 0.68.

TABLE II

| Example No. | Pressure psia (bar) | Inlet Temp. °C. | LHSV $h^{-1}$ | Gas:DMCD mol ratio | Actual Residence Time seconds | Actual Activity | Effective Residence Time seconds | Trans-:cis-CHDM ratio |
| --- | --- | --- | --- | --- | --- | --- | --- | --- |
| 1 | 901 (62.12) | 230 | 0.43 | 338 | 6.7 | 0.68 | 4.6 | 3.0 |
| 2 | 899 (61.98) | 234 | 0.41 | 342 | 6.9 | 0.66 | 4.5 | 3.0 |
| 3 | 899 (61.98) | 234 | 0.41 | 346 | 6.8 | 0.65 | 4.5 | 3.0 |
| 4 | 902 (62.19) | 231 | 0.29 | 404 | 8.4 | 0.54 | 4.5 | 3.0 |
| 5 | 903 (62.26) | 230 | 0.29 | 381 | 8.4 | 0.52 | 4.5 | 3.0 |
| 6 | 901 (62.12) | 233 | 0.31 | 348 | 9.2 | 0.47 | 4.4 | 3.0 |
| 7 | 902 (62.19) | 232 | 0.31 | 339 | 9.5 | 0.48 | 4.4 | 3.0 |

TABLE II-continued

| Example No. | Pressure psia (bar) | Inlet Temp. °C. | LHSV h$^{-1}$ | Gas:DMCD mol ratio | Actual Residence Time seconds | Actual Activity | Effective Residence Time seconds | Trans-:cis-CHDM ratio |
|---|---|---|---|---|---|---|---|---|
| 8 | 903 (62.26) | 233 | 0.31 | 350 | 9.2 | 0.46 | 4.4 | 3.0 |

Notes to Table II:
DMCD = dimethyl 1,4-cyclohexanedicarboxylate
LHSV = liquid hourly space velocity
CHDM = cyclohexanedimethanol
Gas = hydrogen-containing gas containing more than 98% v/v hydrogen.

EXAMPLES 2 TO 8

Using a similar procedure to that described in Example 1 and the same feed solution, 7 further runs were carried out using the copper chromite catalyst (catalyst A in Table I). The runs were designed to determine the expected catalyst life under a variety of operating conditions. The results obtained are summarised in Table II. In each case the vaporous mixture in contact with the catalyst was above the dew point. The actual activity of the catalyst in each Example was determined, prior to or just after taking the readings listed under standard conditions of feed temperature, feed pressure, feedstock flow rate, and hydrogen flow rate.

The data of Examples 1 to 8 were obtained from an extended operating run and show that, despite a considerable decline in catalyst activity over the time span of the Examples, a constant trans-:cis-isomer ratio can be obtained by maintaining a constant effective residence time (ERT).

Examples 1 to 3 show the maintenance of a trans-:cis-isomer ratio in the 1,4-cyclohexanedimethanol product at a feed rate equivalent to a liquid hourly space velocity of 0.41 to 0.43. Minor changes in the pressure and in the hydrogen-containing gas:dimethyl 1,4-cyclohexanedicarboxylate molar ratio suffice to maintain the effective residence time substantially constant and thereby to maintain a substantially constant trans-:cis-isomer ratio in the 1,4-cyclohexanedimethanol product. Over the period of these Examples the conversion of dimethyl 1,4-cyclohexanedicarboxylate averaged 99.0%. From Example 4 onwards the dimethyl 1,4-cyclohexanedicarboxylate feed rate was reduced so as to maintain the conversion of dimethyl 1,4-cyclohexanedicarboxylate at an average of 98.8% over the remainder of the test period. During this time there was a significant decline in catalyst activity as measured under the standard test conditions. However, the trans-:cis-isomer ratio of the 1,4-cyclohexanedimethanol product and the selectivity to 1,4-cyclohexanedimethanol were maintained at a nearly constant level by adjustment of the feed temperature and the hydrogen-containing gas:-dimethyl 1,4-cyclohexanedicarboxylate molar ratio. Only minor changes in feed pressure were necessary over this period.

EXAMPLES 9 TO 17

The effect on dimethyl 1,4-cyclohexanedicarboxylate hydrogenation of altering the operating conditions is summarised in the results listed in Table III. These results demonstrate how the feed conditions can be changed to achieve a selected trans-:cis- isomer ratio in the 1,4-cyclohexanedimethanol product.

TABLE III

| Example No. | Pressure psia (bar) | Inlet Temp. °C. | LHSV h$^{-1}$ | Gas:DMCD mol ratio | Actual Residence Time seconds | Actual Activity | Effective Residence Time seconds | Trans-:cis-CHDM ratio |
|---|---|---|---|---|---|---|---|---|
| 9 | 465 (32.06) | 214 | 0.61 | 311 | 2.7 | 0.89 | 2.4 | 1.6 |
| 10 | 900 (62.05) | 232 | 0.41 | 362 | 6.4 | 0.89 | 5.7 | 3.3 |
| 11 | 900 (62.05) | 217 | 0.62 | 634 | 2.5 | 0.89 | 2.3 | 1.6 |
| 12 | 900 (62.05) | 214.5 | 0.21 | 621 | 7.6 | 0.89 | 6.8 | 3.3 |
| 13 | 678 (46.75) | 231 | 0.41 | 274 | 6.4 | 0.89 | 5.7 | 3.2 |
| 14 | 675 (46.54) | 231 | 0.62 | 272 | 4.3 | 0.89 | 3.8 | 2.5 |
| 15 | 448 (30.89) | 215 | 0.20 | 288 | 8.4 | 0.89 | 7.5 | 2.9 |
| 16 | 658 (45.37) | 231 | 0.21 | 323 | 10.6 | 0.89 | 9.4 | 3.7 |
| 17 | 454 (31.30) | 231 | 0.43 | 188 | 6.0 | 0.89 | 5.4 | 3.0 |

Examples 10, 13 and 17 illustrate the effect of changing the feed pressure and that increasing the feed pressure increases the trans-:cis- isomer ratio obtained. Examples 12, 13 and 16 illustrate the effect of changing the feed rate and that an increased feed rate decreases the trans-:cis- isomer ratio. Examples 9, 15 and 17 illustrate the effect of changing the feed temperature, with increasing feed temperature increasing the trans-:cis- isomer ratio. In all the Examples the hydrogen:diester ratio has been adjusted as appropriate in order to ensure that the product is in the vapour phase.

Example 9 to 17 set out data obtained during an extended hydrogenation run, using the same catalyst charge as was used in Examples 1 to 8. The results of these Examples were obtained over a relatively short time span so that there was little change in actual catalyst activity, as measured under the standard operating conditions, over these Examples. It can be seen that a wide range of trans-:cis- isomer ratios can be obtained in the 1,4-cyclohexanedimethanol product by appropriate variation of the operating conditions. Comparison of Examples 9 and 11 shows that similar low trans-:cis-isomer ratios in the product can be achieved at substantially different pressures by adjustment of the feed temperature and the hydrogen-containing gas:dimethyl 1,4-cyclohexanedicarboxylate molar ratio, even though the dimethyl 1,4-cyclohexanedicarboxylate feed rates were the same. Examples 15 and 17 show that, at similar pressures but at different dimethyl 1,4-cyclohexanedicarboxylate feed rates, adjustment of the temperature and hydrogen-containing gas:dimethyl 1,4-cyclohexanedicarboxylate molar ratio yields similar trans-:cis- isomer ratios in the product. Examples 10 and 13 illustrate the effect of pressure, again under substantially constant conditions, apart from the necessary adjustment of the hydrogen-containing gas:dimethyl 1,4-cyclohexanedicarboxylate molar ratio in order to give the same approach to the dew point in the feed stream. Examples 14 and 16 show the effect of a substantial change in the feed rate of dimethyl 1,4-cyclohexanedicarboxylate at constant feed temperature but with minor variations in pressure and hydrogen-containing gas:dimethyl 1,4-cyclohexanedicarboxylate molar ratio.

In FIG. 3 there is shown a graph showing the relationship between the effective residence time and the trans-:cis- isomer ratio of the resulting 1,4-cyclohexanedimethanol product for two different combinations of feed temperature and feed pressure. In FIG. 3 the continuous line indicates the correlation between the trans-:cis- isomer ratio and effective residence time for a feed pressure of 900 psia (62.05 bar) and a feed temperature of 240° C. while the broken line is the corresponding line for a feed pressure of 450 psia (31.03 bar) and a feed temperature of 215° C. Similar lines can be drawn for other combinations of feed temperature and feed pressure. From such graphs a person skilled in the art can select the appropriate operating conditions needed to achieve constant effective residence time and thus a substantially constant trans-:cis- isomer ratio.

We claim:

1. A continuous process for the production of 1,4-cyclohexanedimethanol having a desired or predetermined trans-:cis- isomer ratio by catalytic hydrogenation of dialkyl 1,4-cyclohexanedicarboxylate in the presence of an ester hydrogenation catalyst selected from copper-containing catalysts and Group VIII metal-containing catalysts, which process is capable of being operated for an extended period of time during which the hydrogenation catalyst declines in catalytic activity, said process comprising:

(a) providing a hydrogenation zone containing a charge of a granular hydrogenation catalyst selected from copper-containing catalysts and Group VIII metal-containing catalysts capable of catalysing the hydrogenation of esters;
   (b) determining a Reference Activity (RA) of the granular hydrogenation-catalyst by measuring the extent of conversion of the dialkyl 1,4-cyclohexanedicarboxylate to 1,4-cyclohexanedimethanol in passage of a reaction mixture comprising the dialkyl 1,4-cyclohexanedicarboxylate and a hydrogen-containing gas through the granular hydrogenation catalyst at a preselected feed temperature, feed pressure, dialkyl 1,4-cyclohexanedicarboxylate feed rate, and hydrogen-containing gas:dialkyl 1,4-cyclohexanedicarboxylate molar ratio;
   (c) determining an Effective Residence Time (ERT) for contact of the reaction mixture at the preselected feed temperature and feed pressure with the granular hydrogenation catalyst at the reference activity thereof which produces 1,4-cyclohexanedimethanol having the desired trans-:cis- isomer ratio;
   (d) forming a vaporous feed stream comprising the dialkyl 1,4-cyclohexanedicarboxylate and a hydrogen-containing gas having a preselected hydrogen-containing gas:dialkyl 1,4-cyclohexanedicarboxylate molar ratio;
   (e) feeding the vaporous feed stream to the hydrogenation zone at a constant temperature of from about 150° C. to about 350° C. and which is above the dew point of the feed stream and at a constant pressure in the range of from about 150 psia (about 10.34 bar) to about 2000 psia (about 137.90 bar) at a rate which corresponds to an Actual Residence Time (ART) of the feed stream in contact with the catalyst which yields 1,4-cyclohexanedimethanol of the desired trans-:cis- isomer ratio;
   (f) recovering from the hydrogenation zone a product stream containing 1,4-cyclohexanedimethanol;
   (g) monitoring the Actual Activity (AA) of the granular hydrogenation catalyst with passage of time by measuring the extent of conversion of the dialkyl 1,4-cyclohexanedicarboxylate to 1,4-cyclohexanedimethanol under the actual operating conditions of feed temperature, feed pressure, dialkyl 1,4-cyclohexanedicarboxylate feed rate, and hydrogen-containing gas:dialkyl 1,4-cyclohexanedicarboxylate molar ratio; and
   (h) adjusting at least one feed condition of the vaporous feed stream to the hydrogenation zone selected from
      (i) the dialkyl 1,4-cyclohexanedicarboxylate feed rate and
      (ii) the hydrogen-containing gas:dialkyl 1,4-cyclohexanedicarboxylate molar-ratio while maintaining the feed stream above its dew point to provide an Actual Residence Time (ART) of the vaporous feed stream in contact with the catalyst which corresponds to the Effective Residence Time (ERT) required to provide 1,4-cyclohexanedimethanol having the desired trans-:cis-isomer ratio in accordance with the relationship:

$$ART = \frac{ERT \times RA}{AA}$$

wherein the dialkyl cyclohexanedicarboxylate is selected from di-($C_1$ to $C_4$ alkyl) cyclohexanedicarboxylates.

2. A process according to claim 1, in which the dialkyl cyclohexanedicarboxylate is trans-dimethyl 1,4-cyclohexanedicarboxylate.

3. A process according to claim 1, in which the dialkyl cyclohexanedicarboxylate is cis-dimethyl 1,4-cyclohexanedicarboxylate.

4. A process according to claim 1, in which the dialkyl 1,4-cyclohexanedicarboxylate comprises a mixture of the cis- and trans- isomers of dimethyl cyclohexanedicarboxylate.

5. A process according to claim 1, in which the hydrogen-containing gas:dialkyl cyclohexanedicarboxylate mole ratio in the vaporous mixture is in the range of from about 200:1 to about 1000:1.

6. A process according to claim 1, in which the feed temperature to the hydrogenation zone is in the range of from about 150° C. to about 300° C.

7. A process according to claim 6, in which the feed temperature to the hydrogenation zone is in the range of from about 200° C. to about 260° C.

8. A process according to claim 6, in which the feed pressure is in the range of from about 450 psia (about 31.03 bar) to about 1000 psia (about 68.95 bar).

9. A process according to any one of claims 1 to 8, in which the catalyst is selected from reduced manganese promoted copper catalysts, reduced copper chromite catalysts, and reduced promoted copper chromite catalysts.

10. A process according to claim 9, in which the catalyst comprises not more than about 15% by weight of at least one promoter selected from barium, manganese, and mixtures thereof.

11. A process according to claim 6, in which the dialkyl 1,4-cyclohexanedicarboxylate is supplied at a rate corresponding to a liquid hourly space velocity of from about 0.05 to about 4.0 h$^{-1}$.

12. A process according to claim 6, in which the effective residence time is selected to yield a 1,4-cyclohexanedimethanol product having a trans-:cis- isomer ratio of from about 2.0:1 to about 3.84:1.

13. A process according to claim 6, in which in step (h) adjustment of the at least one feed condition includes the step of adjusting the dialkyl 1,4-cyclohexanedicarboxylate feed rate.

14. A continuous process for the production of 1,4-cyclohexanedimethanol having a desired or predetermined trans-:cis- isomer ratio of from about 2.0:1 to about 3.84:1 by catalytic hydrogenation of dimethyl 1,4-cyclohexanedicarboxylate in the presence of an ester hydrogenation catalyst, which process is capable of being operated for an extended period of time during which the hydrogenation catalyst declines in catalytic activity, said process comprising:

(a) providing a hydrogenation zone containing a charge of a granular hydrogenation catalyst selected from reduced copper chromite catalysts wherein the Cu:Cr weight ratio is from about 0.1:1 to about 4:1; reduced, copper chromite catalysts wherein the Cu:Cr weight ratio is from about 0.1:1 to about 4:1 promoted with from about 0.1% by weight up to 15% by weight of barium, manganese or a mixture of barium and manganese; or reduced manganese promoted copper catalysts wherein the Cu:Mn weight ratio is from about 2:1 to about 10:1 capable of catalysing the hydrogenation of esters;

(b) determining a Reference Activity (RA) of the granular hydrogenation catalyst by measuring the extent of conversion of the dimethyl 1,4-cyclohexanedicarboxylate to 1,4-cyclohexanedimethanol in passage of a reaction mixture comprising dimethyl 1,4-cyclohexanedicarboxylate and a hydrogen-containing gas through the granular hydrogenation catalyst at a preselected feed temperature, feed pressure, dimethyl 1,4-cyclohexanedicarboxylate feed rate, and hydrogen-containing gas:dimethyl 1,4-cyclohexanedicarboxylate molar ratio;

(c) determining an Effective Residence Time (ERT) for contact of the reaction mixture at the preselected feed temperature and feed pressure with the granular hydrogenation catalyst at the reference activity thereof which produces 1,4-cyclohexanedimethanol having the desired trans-:cis- isomer ratio of from about 2.0:1 to about 3.84:1;

(d) forming a vaporous feed stream comprising dimethyl 1,4-cyclohexanedicarboxylate and a hydrogen-containing gas having a preselected hydrogen-containing gas:dimethyl 1,4-cyclohexanedicarboxylate molar ratio;

(e) feeding the vaporous feed stream to the hydrogenation zone at a constant temperature of from about 150° C. to about 300° C. and which is above the dew point of the feed stream and at a constant pressure in the range of from about 450 psia (about 31.03 bar) to about 1000 psia (about 68.95 bar) at a rate which corresponds to an Actual Residence Time (ART) of the feed stream in contact with the catalyst which yields 1,4-cyclohexanedimethanol of the desired trans-:cis- isomer ratio of from about 2.0:1 to about 3.84:1;

(f) recovering from the hydrogenation zone a product stream containing 1,4-cyclohexanedimethanol;

(g) monitoring the Actual Activity (AA) of the granular hydrogenation catalyst with passage of time by measuring the extent of conversion of the dimethyl 1,4-cyclohexanedicarboxylate to 1,4-cyclohexanedimethanol under the actual operating conditions of feed temperature, feed pressure, dimethyl 1,4-cyclohexanedicarboxylate feed rate, and hydrogen-containing gas:dimethyl 1,4-cyclohexanedicarboxylate molar ratio; and (h) adjusting at least one feed condition of the vaporous feed stream to the hydrogenation zone selected from
(i) the dimethyl 1,4-cyclohexanedicarboxylate feed rate and
(ii) the hydrogen-containing gas:dialkyl 1,4-cyclohexanedicarboxylate molar-ratio while maintaining the feed stream above its dew point to provide an Actual Residence Time (ART) of the vaporous feed stream in contact with the catalyst which corresponds to the Effective Residence Time (ERT) required to provide 1,4-cyclohexanedimethanol having the desired trans-:cis- isomer ratio in accordance with the relationship:

$$ART = \frac{ERT \times RA}{AA}.$$

15. A process according to claim 14 wherein step (e) comprises feeding the vaporous feed stream to the hydrogenation zone at a constant temperature of from about 200° C. to about 260° C. and which is above the dew point of the feed stream and at a constant pressure in the range of from about 450 psia (about 31.03 bar) to about 1000 psia (about 68.95 bar).

* * * * *